United States Patent
Shen et al.

(10) Patent No.: US 10,082,600 B2
(45) Date of Patent: Sep. 25, 2018

(54) METHODS OF CALIBRATION TRANSFER FOR A TESTING INSTRUMENT

(75) Inventors: Jing Shen, Houston, TX (US);
Christopher Jones, Houston, TX (US);
Dingding Chen, Plano, TX (US);
Michael T. Pelletier, Houston, TX (US); Robert Atkinson, Richmond, TX (US); David Perkins, Irmo, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 671 days.

(21) Appl. No.: 14/364,119

(22) PCT Filed: Dec. 16, 2011

(86) PCT No.: PCT/US2011/065373
§ 371 (c)(1),
(2), (4) Date: Jun. 10, 2014

(87) PCT Pub. No.: WO2013/089764
PCT Pub. Date: Jun. 20, 2013

(65) Prior Publication Data
US 2014/0309959 A1    Oct. 16, 2014

(51) Int. Cl.
*G01V 13/00* (2006.01)
*G01N 33/24* (2006.01)
*G01N 21/27* (2006.01)

(52) U.S. Cl.
CPC ........... *G01V 13/00* (2013.01); *G01N 21/274* (2013.01); *G01N 33/241* (2013.01); *G01N 2201/129* (2013.01); *G01N 2201/1296* (2013.01)

(58) Field of Classification Search
CPC .. G01N 21/274; G01N 21/359; G01N 21/276; G01J 3/28; G01J 3/02; A61B 5/0075
USPC .............. 250/252.1, 339.08, 339.09; 356/51, 356/243.1, 300; 702/6, 14, 19, 25, 85, 702/105
See application file for complete search history.

(56) References Cited

U.S. PATENT DOCUMENTS

| | | | |
|---|---|---|---|
| 4,866,644 A | | 9/1989 | Shenk et al. |
| 5,838,008 A | * | 11/1998 | Esler .................. G01J 3/28 |
| | | | 250/339.07 |

(Continued)

OTHER PUBLICATIONS

Feudale, R.N. et al., "Transfer of multivariate calibration models: a review", Chemometrics and Intelligent Laboratory Systems, vol. 64, No. 2, Elsevier Science Publishers B.V. (Nov. 28, 2002), pp. 181-192.

(Continued)

*Primary Examiner* — Roy Y Yi
*Assistant Examiner* — Jeffrey Aiello
(74) *Attorney, Agent, or Firm* — Benjamin Fite; Baker Botts L.L.P.

(57) ABSTRACT

A method of calibration transfer for a testing instrument includes: collecting a first sample; generating a standard response of a first instrument based, at least in part, on the first sample; and performing instrument standardization of a second instrument based, at least in part, on the standard response of the first instrument. Data corresponding to a second sample is then obtained using the second instrument and a component of the second sample is identified based, at least in part, on a calibration model.

20 Claims, 21 Drawing Sheets

(56) References Cited

U.S. PATENT DOCUMENTS

| | | | | |
|---|---|---|---|---|
| 5,918,191 | A * | 6/1999 | Patel | G06Q 10/06 702/100 |
| 6,072,576 | A * | 6/2000 | McDonald | C08F 210/12 250/339.08 |
| 7,277,810 | B2 * | 10/2007 | Schumacher | G01R 35/00 702/104 |
| 8,652,799 | B2 * | 2/2014 | Bellemare | G01N 33/5097 435/29 |
| 2005/0029457 | A1 * | 2/2005 | Long | G01N 21/274 250/339.08 |
| 2006/0142955 | A1 * | 6/2006 | Jones | E21B 47/102 702/32 |
| 2008/0290279 | A1 * | 11/2008 | Juhl | G01J 3/28 250/339.08 |
| 2012/0232707 | A1 * | 9/2012 | Jones | G01N 21/274 700/283 |

OTHER PUBLICATIONS

Mohsen Kompany-Zareh, Frans van den Berg, "Multi-way based calibration transfer between two Raman spectrometers," Analyst, vol. 135 (Apr. 19, 2010), pp. 1382-1388.

Gislason, J. et al., "Calibration transfer of chemometric models based on process nuclear magnetic resonance spectroscopy," Applied Spectroscopy, vol. 55, No. 11 (Nov. 2001), pp. 1553-1560.

International Search Report and Written Opinion issued in PCT Application No. PCT/US2011/065373 dated Oct. 5, 2012, 10 pages.

International Preliminary Report on Patentability issued in PCT Application No. PCT/US2011/065373 dated Mar. 12, 2014, 21 pages.

Xu, Rui et al., "Survey of Clustering Algorithms," IEEE Transactions on Neural Networks, vol. 16, No. 3 (May 2005), 34 pages.

Cogdill, Robert P. et al., "Using NIR Spectroscopy as an Integrated PAT Tool" in Spectroscopy, vol. 19 (12), (Dec. 2004), 6 pages.

* cited by examiner ies of a sample that may be implemented in whole or in part as a PVT (pressure volume temperature) analysis system, according to certain embodiments of the present disclosure.
METHODS OF CALIBRATION TRANSFER FOR A TESTING INSTRUMENT

CROSS-REFERENCE TO RELATED APPLICATION

This application is a U.S. National Stage Application of International Application No. PCT/US2011/065373 filed Dec. 16, 2011, and which is hereby incorporated by reference in its entirety.

BACKGROUND

The present disclosure relates to fluid analysis and, more particularly, to methods of calibration transfer to a testing instrument.

In subterranean well drilling and completion, tests on formations penetrated by a wellbore are typically performed in order to determine geological or other physical properties of the formation and fluids contained therein. For example, parameters such as permeability, porosity, fluid resistivity, temperature, pressure and saturation pressure may be determined. These and other characteristics of the formation and fluid contained therein may be determined by performing tests on the formation before the well is completed.

To evaluate prospects of an underground hydrocarbon reserve, a representative sample of the fluid may be captured for detailed analysis. In a typical sampling procedure, a sample of the formation fluids may be obtained by lowering a sampling tool having a sampling chamber into the wellbore on a conveyance such as a wireline, slick line, coiled tubing, jointed tubing or the like. When the sampling tool reaches the desired depth, one or more ports are opened to allow collection of the formation fluids. The ports may be actuated in a variety of ways such as by electrical, hydraulic or mechanical methods. Once the ports are opened, formation fluids travel through the ports and a sample of the formation fluids is collected within the sampling chamber of the sampling tool. After the sample has been collected, the formation fluid sample may be analyzed.

Competitive reservoir formation testing requires determination of primary fluid components in the field. A filter spectrometer may be built into a downhole tool to generate a sample spectrum, and a data processor may be used based on calibrated multivariate predictive models. However, multivariate calibration of multiple instruments can be a challenge, as the calibration can be very sensitive to small variations in the wavelengths and absorbance, for example. The calibrations developed on one instrument at a standard calibration lab, for example, can generally not transfer to a second instrument of the same type to be used in the field without some adjustment to either the spectral data or the calibration. Accordingly, there is a need for robust calibration transfer to effectively address these challenges.

FIGURES

Some specific exemplary embodiments of the disclosure may be understood by referring, in part, to the following description and the accompanying drawings.

Figure 1:
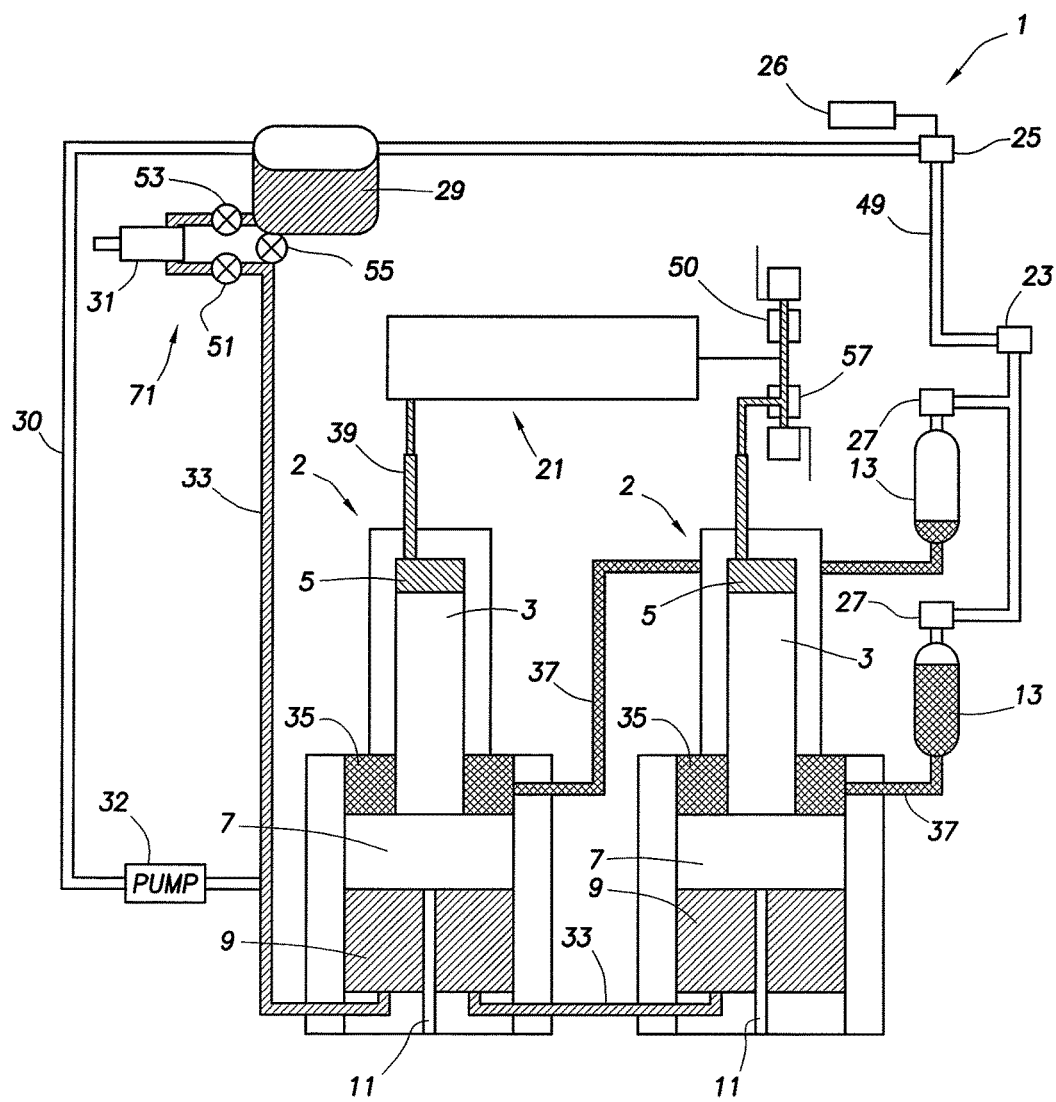
FIG. 1 shows an apparatus for acquiring physical properties of a sample that may be implemented in whole or in part as a PVT (pressure volume temperature) analysis system, according to certain embodiments of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates to fluid analysis and, more particularly, to methods of calibration transfer to a testing instrument.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented in which the tool is made suitable for testing, retrieval and sampling along sections of the formation. Embodiments may be implemented with various testing tools that, for example, may be conveyed through flow passage in tubular string or using a wireline, slickline, coiled tubing, downhole robot or the like. The system of present disclosure may be suited for use with a modular downhole formation testing tool, such as the Reservoir Description Tool (RDT) by Halliburton, for example. Devices and methods in accordance with certain embodiments may be used in one or more of wireline, measurement-while-drilling (MWD) and logging-while-drilling (LWD) operations.

Certain embodiments of the present disclosure may be implemented at least in part with an information handling system. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a computer, a network storage device, or any other suitable device and may vary in size, shape, performance, and functionality. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display.

Certain embodiments of the present disclosure may be implemented at least in part with computer-readable media. For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

Competitive reservoir formation testing requires determination of primary fluid components in the field. In certain embodiments, that determination may be made in real-time. A filter spectrometer may be built into an RDT to generate a sample spectrum, and a data processor may be used to make quick component prediction based on the calibrated multivariate predictive models. Certain embodiments according to the present disclosure provide for robust calibration transfer. Certain embodiments provide for calibration transfer from a spectroscopic database to a specific tool filter spectrometer, which may include using a database, a neural network or any appropriate pattern recognition or classification system to pick the most appropriate samples, then transferring to a specific tool response, and using tuning parameters for instrument standardization. The present disclosure, which includes database development, experimental design, calibration model optimization, and determination of suitable methods for calibration transfer, may be described herein as certain embodiments for a downhole filter spectrometer, but may be generally applied to a variety of cross instrument response measurements.

FIG. 1 shows an apparatus 1 for acquiring physical properties of a sample that may be implemented in whole or in part as a PVT (pressure volume temperature) analysis system, according to certain embodiments of the present disclosure. The combination of pneumatic and hydraulic operation of the apparatus may allow for use in the field. Coupled with computer control, the apparatus may be nearly autonomous, running experiments unattended for hours and to completion. Certain embodiments may not utilize large mechanical or motor driven pumps.

The apparatus 1 has one or more pressure intensifiers 2 (two are shown). A sample piston 3 coupled to a hydraulic support piston 7 may be disposed within each pressure intensifier 2. Drive fluid 35 and hydraulic support fluid 9 may be shown on opposite sides of the hydraulic support piston 7. A piston position measurement device 11 may be located in the pressure intensifier 2 to measure the position change of the hydraulic support piston 7 or sample piston 3.

Changes in the piston positions may be used to calculate such properties as viscosity, total sample volume, compressibility and fluid flow rate.

The sample piston 3 may be in contact with a sample 5. The sample 5 can be made up of a liquid, gas, or both. A sample fluid line 39 may contain the sample 5 as it moves from the pressure intensifier 2 through a sample manifold 21. A hydraulic support fluid line 33 may carry the hydraulic support fluid 9 between the pressure intensifiers 2 and a hydraulic support fluid reservoir 29. A hydraulic pump 32 may be connected into the hydraulic support fluid line 33. A hydraulic pump suction line 30 may be connected to the hydraulic support fluid reservoir 29.

A constant volume discharge cylinder 31 may be positioned between the hydraulic support fluid reservoir 29 and the pressure intensifiers 2, which may make up the constant volume metering assembly 71 that controls the release of hydraulic support fluid 9 from the hydraulic support fluid line 33. The constant volume discharge cylinder 31 may contain a piston (not shown) which discharges the hydraulic support fluid 9. The piston may be spring loaded or pneumatically activated, for example. A constant volume assembly inlet valve 51 with an actuator, a constant volume assembly outlet valve 53 with an actuator, and a fast fill/drain valve 55 may be positioned in the hydraulic support fluid line 33. A pneumatic source valve 25 may be located in a pneumatic source line 49. The pneumatic source line 49 carries a gas to one or more drive fluid reservoirs 13. A pneumatic valve 27 may be positioned adjacent to the drive fluid reservoirs 13. A pressure regulator 23 may be positioned in the pneumatic source line 49. The drive fluid 35 may be carried by one or more drive fluid lines 37 between the pressure intensifiers 2 and the drive fluid reservoirs 13. The entire apparatus 1 may be temperature controlled. For example, a circulated water bath (not shown) may encompass the apparatus 1 in order to operate the apparatus 1 under a constant temperature.

The hydraulic support fluid reservoir 29 may maintain the hydraulic support fluid 9 controlled by the constant volume metering assembly 71. The fast drain/fill valve 55 may be optional and allows for the quick draining or filling of hydraulic support fluid 9 into the hydraulic support fluid reservoir 29. In order to manipulate hydraulic support fluid 9 to and from the apparatus 1, pneumatic control lines may actuate the inlet 51 and outlet 53 valves, which discharges a constant volume into the constant volume discharge cylinder 31. The exact amount introduced or removed can be measured by monitoring the piston position change with the piston position measurement device 11. The addition of the hydraulic pump 32 may allow the re-pressurization of the system. This is necessary if the remainder of a test is to be conducted at a lower temperature, the tests are to be repeated, to compensate for the removal of sample for composition testing or to properly conduct depletion tests.

The pneumatic source valve 25 may allow for the introduction of a pneumatic source 26. The pneumatic source 26 for the apparatus 1 may be nitrogen or compressed air. Nitrogen provides the distinct advantage of not supporting combustion as compared to compressed air, which may be more readily available at field locations. The pneumatic source lines 49 may connect the pneumatic source 26 to the drive fluid reservoirs 13. A pressure regulator 23 may control the application of the pneumatic source 26. The drive fluid reservoirs 13 may work in opposite directions as they supply drive fluid 35 to the sample piston 3 side of the pressure intensifiers 2. One or more pneumatic valves 27 (two are shown) in fluid communication with at least one of the drive fluid reservoirs 13 may be vented at opposite times to push or release drive fluid 35. The pneumatic valves 27 may be automated.

Figure 2:
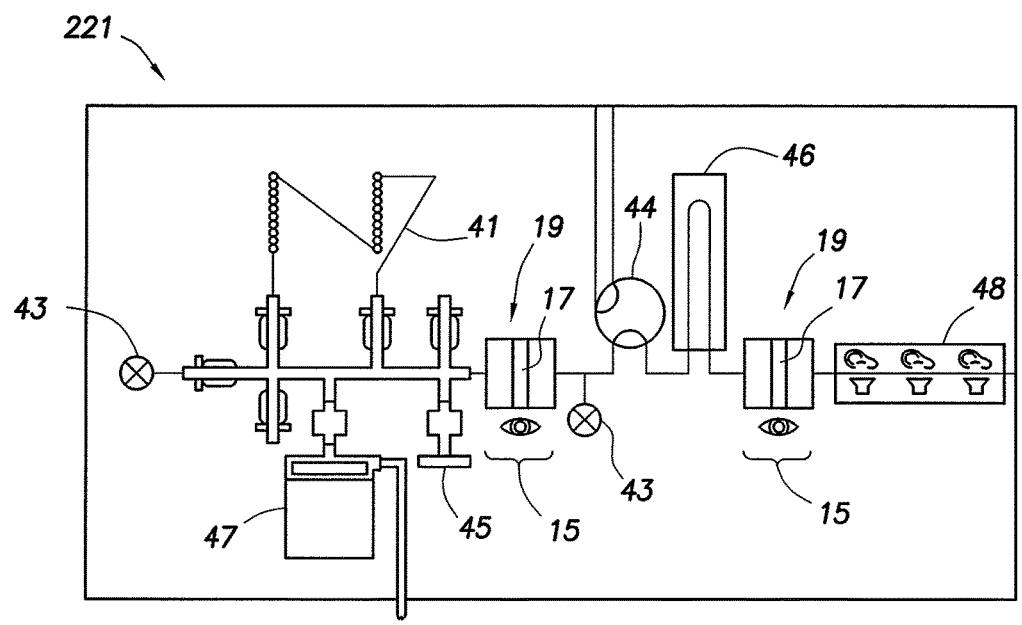
FIG. 2 shows a sample manifold which may be used in the apparatus of FIG. 1, according to certain embodiments of the present disclosure.

FIG. 2 shows a sample manifold 221 which may be used in the apparatus of FIG. 1, according to certain embodiments of the present disclosure. The sample manifold 221 may contain a viscosity coil 41 with a viscosity coil bypass valve 47. The viscosity coil 41 may be made up of capillary tubing of a measured length and diameter. The viscosity coil bypass valve 47 may be automated and allows for the sample 5 (shown in FIG. 1) to flow independent of the viscosity coil 41. Pressure gauges 43 may be located on opposite sides of the viscosity coil 41 to measure pressure changes of the sample 5. A sample inlet valve 45 may allow for the introduction of the sample 5 into the sample manifold 21. A series of sensors may be installed to measure the properties of the sample 5, including, but not limited to, one or more optical cells 15, one or more sampling valves 44, one or more density sensors 46, and one or more acoustical sensors 48. The optical cell 15 may be positioned in the sample fluid line 39 and may contain a viewing window 17 and work in conjunction with a light source 19 for viewing or measuring. Sample fluids may be metered out of sample manifold 221 by a sample constant volume valve assembly 50. A sample isolation valve 57 may connect the sample manifold 21 to the pressure intensifier 2 (shown in FIG. 1). The sampling valves 44 may allow a small fixed volume sample to be removed from the single phase sample stream (gas or oil) and directly delivered to other analytical instruments not shown.

Referring now to FIGS. 1 and 2, the sample lines 39 may contain the flow of sample 5 between pressure intensifiers 2. The sample lines 39 may connect with a sample manifold 21, containing valves and coils to manipulate the sample 5. The sample inlet valve 45 may act as a port to introduce or remove the sample 5. The sample 5 may be introduced under controlled conditions and during an experimental run. The sample 5 may be pushed through the viscosity coil 41 in order to measure the viscosity. The direction of flow may be governed by the pneumatic control valves 27. The flow rate of the sample 5 across the viscosity coil 41 can be measured by manipulating time and position measurements from the piston measurement device 11. The sample flow rate can be increased or decreased by changing the set point of the pressure regulator 23. The differential pressure may be monitored between the pressure gauges 43 and flow rate may be measured based on movement of one or more of the pistons 3, 7, and the piston of the constant volume discharge cylinder 31, in order to calculate viscosity based on Poiseuille's Law.

The cylinder isolation valve 57 may allow samples to be segregated where a liquid portion of the sample 5 is below the cylinder isolation valve 57, so that a gas portion of the sample 5 may be removed. The sample constant volume assembly 50 may be used to remove the sample 5 or a portion of the sample 5 in a controlled manner. The sample constant volume assembly 50 may operate in a similar manner to the constant volume metering assembly 71 discussed and described above. Pressure can be maintained on the sample 5, for example, by injecting hydraulic support fluid 9 using the hydraulic pump 32. The process of removing a portion or the totality of the gas phase from the sample 5 at regular pressure increments may be depletion testing. This may model the behavior of reservoir fluids as they are produced.

The optical cell 15 may have a viewing window 17 to observe the sample and a light source 19. The light transmitted from the light source 19 may change from low intensity to high intensity in the presence of flowing gas and again back to low intensity when the liquid phase is again being displaced. The light source 19 may be a simple bulb, or as exotic as an electromagnetic radiation source. The detection windows of the optical cell may be fitted with a simple observation lens, other radiation detectors, or an analytical instrument such as a spectrometer or X-ray fluorometer. The illumination axis and detection axis for the optical cell may or may not be collinear. In one embodiment, the light source 19 may emit ultraviolet radiations, visible light, infrared radiations or X-ray radiations.

The sample fluid lines 39 may also be coupled to additional sensors. Examples of such sensors may include, but are not limited to density sensors 46, optical cells 15, and acoustical sensors 48. The inclusion of the optical cells 15 may allow the spectrometric identification of hydrocarbon families and the detection of agglomerated asphaltinic and waxy components in the sample 5. The acoustical sensors 48 may be used to detect both hydrocarbon and inorganic particulates, determine sonic velocities and may measure adiabatic compressibility of the sample 5.

Figure 3:
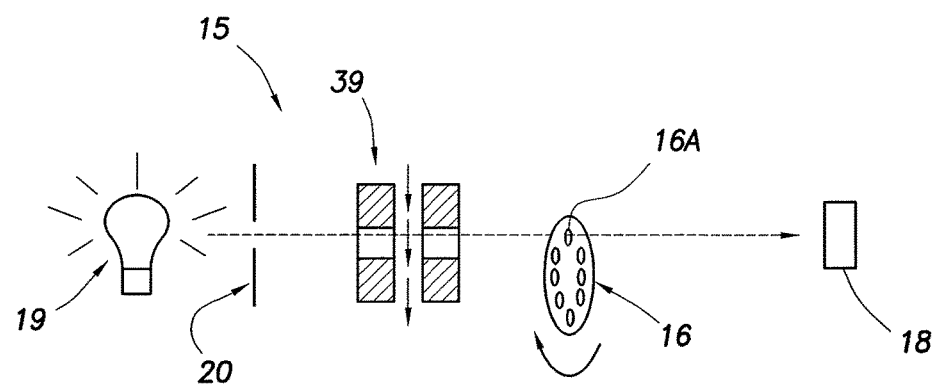
FIG. 3 shows an optical cell implemented with a filter wheel, in accordance with certain embodiments of the present disclosure.

FIG. 3 shows an optical cell 15 implemented with a filter wheel 16, in accordance with certain embodiments of the present disclosure. The light source 19 may be disposed so that an illumination axis and/or a detection axis are aligned with a slit 20, the sample line 39, a filter wheel 16, and an optical sensor 18. In certain embodiments, the optical sensor 18 may include one or more FTIR (Fourier Transform Infrared) sensors. The filter wheel 16 may include one or more filters 16A and may be adjustable to expose a particular filter 16A to the illumination axis and/or the detection axis.

In accordance with an embodiment of the present disclosure, a global oil library may be developed and stored in one or more spectroscopic databases. Oil sample data may be from all over the world, thereby ensuring a diversity of physical and chemical properties as well as geologic histories. In certain embodiments, a high-temperature, high-pressure (for example, without limitation, 350° F. and 20,000 psi) automated PVT system implementing the apparatus 1 in whole or in part may have access to the one or more spectroscopic databases. The one or more spectroscopic databases may include visible, near-IR (infrared), and mid-IR spectra (e.g., 400-5000 nm) associated with the physical properties of petroleum, including bubble point, phase envelope, density, viscosity, compressibility, and thermal expansion, which may be characterized in the PVT system. The one or more spectroscopic databases may include the visible and IR spectra of oil samples associated with SARA (saturates, aromatics, resins and asphaltenes) compositions, dissolved methane, ethane, propane, butane, pentane, hexane, higher hydrocarbons, carbon dioxide, water, hydrogen sulfide concentrations, GOR (gas/oil ratio), physical properties including density and PVT properties of fluid for normal oilfield temperature and pressure combinations.

The PVT system may be used to reconstitute dead oil compositions (loss of light end components at surface conditions) to original reservoir live oil states, reconstitute one or more analyses of original live oil properties, and/or directly analyze live formation fluids captured. Reconstitution components may be adjusted or added as needed. The PVT system may have a computer-controlled capability of adding pure components of methane, ethane, propane, carbon dioxide, water, hydrogen sulfide, and a natural distribution of hydrocarbons from butane to dodecane.

As a non-limiting example of spectra data collection and development, in certain embodiments spectra data collected on the PVT system's FTIR sensors may be linear in wavenumbers from 10,000 cm^-1 to 1,500 cm^-1 with a resolution of 32 cm^-1 for a total of 551 channels. Resolution and wavelength range may be adjusted based on choice of optical sensors. And, as a non-limiting example, a total of 64 samples may be averaged to generate a single spectrum; temperature range may be from 150° F. to 250° F.; pressure range may be from 3,000 psi to 12,000 psi. Other operational ranges, such as to 400° F. and 30,000 psi and higher are possible.

Averaged spectra data may be filtered for type II outliers and then averaged for a global SNR (signal-to-noise ratio) of approximately 10,000:1, for example. Spectra data may be interpolated to a wavelength linear axis from 1,001.7495 to 6,679 nm in 2,048 channels. As a non-limiting example, such interpolation may be performed using the MATLAB® function interp1. The Piecewise Cubic Hermite Interpolating Polynomial (PCHIP) option may be used for the interpolation. However, linear interpolation may be suitable for some particularly noisy data.

In certain embodiments, a large set of air spectra data may also be recorded as reference spectra data. The reference spectra data may be filtered and interpolated in the same way as the oil spectra data. The reference spectra data may be translated to a baseline zero by subtraction of an average of baseline points within the spectra. Dividing the air transmittance spectra by the oil transmittance spectra may yield a fractional transmittance (ft). As a non-limiting example, the fractional transmittance may represented by a M-by-2048 matrix, with M being the number of spectra in the database and 2048 being the number of channels:

| $ft1_1$ | $ft1_2$ | $ft1_3$ | ... | $ft1_{2048}$ |
|---|---|---|---|---|
| $ft2_1$ | $ft2_2$ | $ft2_3$ | ... | $ft2_{2048}$ |
| $ft3_1$ | $ft3_2$ | $ft3_3$ | ... | $ft3_{2048}$ |
| ⋮ | ⋮ | ⋮ | ⋮ | ⋮ |
| $ftM_1$ | $ftM_2$ | $ftM_3$ | ... | $ftM_{2048}$ |

A negative common logarithm of the fractional transmittance may yield an absorbance spectrum. The background effects such as window dirtying may be assumed to be constant. For example, a typical baseline may be from 1,500 nm to 1,600 nm.

Figure 4:
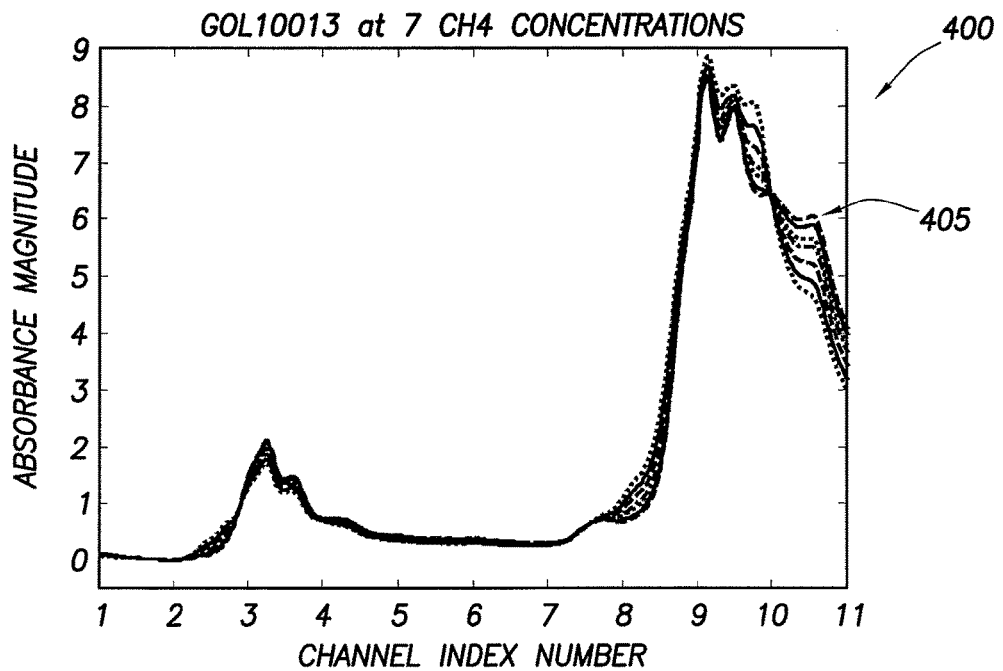
FIG. 4 is a graph of exemplary IR spectra, in accordance with certain embodiments of the present disclosure.

FIG. 4 is a graph 400 of exemplary IR spectra. The example of FIG. 4 may be a non-limiting exemplary database spectra and may correspond to IR spectra of a North Sea oil at 150° F., 6,000 psi, and 9,000 psi, with some spectra moved for clarification. Each line 405 indicates one concentration condition of CH4. The darkest lines 405 are spectra of dead crude oil, and the other lighter-shaded lines are spectra under different concentrations of dissolved CH4.

According to certain embodiments, an interference filter set in a spectrometer or other sensor configuration may be developed with a genetic algorithm (GA) to achieve optimal parameters, such as robustness to temperature effects and vibration, and to facilitate calibration transfer. Gaussian basis functions may be employed as part of the filter set development. However, it should be understood that other theoretical functions, including complex waveforms, may be used.

Figure 5:
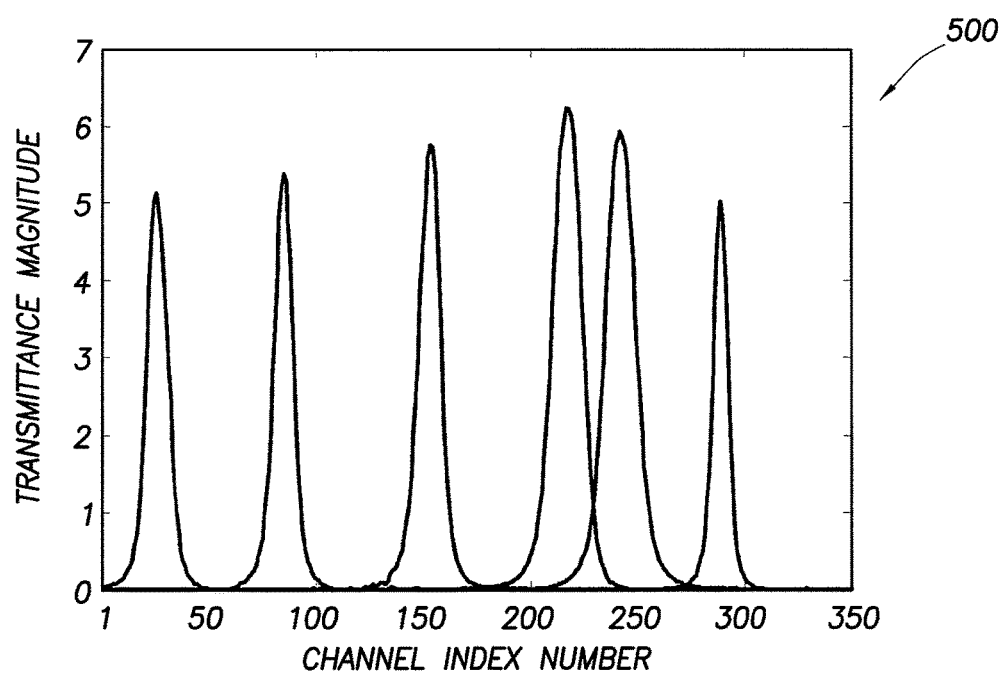
FIG. 5 is an example graph of Gaussian basis functions of an interference filter set in a spectrometer, in accordance with certain embodiments of the present disclosure.

FIG. 5 is an example graph 500 of Gaussian basis functions of an interference filter set in a spectrometer. In certain exemplary embodiments, a transmittance spectrum of a particular light source (I0) may be measured and interpolated in 2048 channels. As indicated by Equation 1, the interference filters' Gaussian basis function (FF) multiplied by the band pass transmittance spectrum (outband) may yield the I0c channel data:

$$I0c_N = I0_1*FFN_1*outb_1 + I0_2*FFN_2*outb_2 + I0_3*FFN_3*outb_3 + \ldots + I0_{2048}*FFN_{2048} \times outb_{2048}$$ (Equation 1)

With N being the number of interference filters, I0 may a 1-by-2048 matrix, for example:

| $I0_1$ | $I0_2$ | $I0_3$ | ... | $I0_{2048}$ |
|---|---|---|---|---|

FF may be an N-by-2048 matrix:

| $FF1_1$ | $FF1_2$ | $FF1_3$ | ... | $FF1_{2048}$ |
|---|---|---|---|---|
| $FF2_1$ | $FF2_2$ | $FF2_3$ | ... | $FF2_{2048}$ |
| ⋮ | ⋮ | ⋮ | ⋮ | ⋮ |
| $FFN_1$ | $FFN_2$ | $FFN_3$ | ... | $FFN_{2048}$ |

Outband may be a 1-by-2048 matrix:

| $outb_1$ | $outb_2$ | $outb_3$ | ... | $outb_{2048}$ |
|---|---|---|---|---|

I0c channel data may be a 1-by-N matrix:

| $I0c_1$ | $I0c_2$ | $I0c_3$ | ... | $I0c_N$ |
|---|---|---|---|---|

The air spectrum for a particular optical cell (Iairc) may be measured, which also may be an N-by-1 matrix:

| $Iairc_1$ | $Iairc_2$ | $Iairc_3$ | ... | $Iairc_N$ |
|---|---|---|---|---|

Filter temperature effects may be either calculated or measured and used to generate a theoretical transmission spectrum (mathematically treated as a vector) as a function of temperature. Equation 2 gives the theory tool channel data:

$$\text{theory tool data}M \text{ channel}N = ftM_1*I0_1*FFN_1*outb_1 + ftM_2*I0_2*FFN_2*outb_2 + ftM_3*I0_3*FFN_3*outb_3 + \ldots ftM_{2048}*I0_{2048}*FFN_{2048}*outb_{2048}$$ (Equation 2)

The theory tool channel data which may be a (M-by-N) matrix M may be a number of database spectra:

| theory tool data1 channel1 | theory tool data1 channel2 | ... | theory tool data1 channelN |
|---|---|---|---|
| theory tool data2 channel1 | theory tool data2 channel2 | ... | theory tool data2 channelN |
| . | . | . | . |
| . | . | . | . |
| . | . | . | . |
| theory tool dataM channel1 | theory tool dataM channel2 | ... | theory tool dataM channelN |

The theoretical absorbance spectra of the tool may be generated by Equation 3.

$$\text{theoretical absorbance} = -\log_{10}(Iairc_N/I0cN*(\text{theory tool data}M \text{ channel}N)/IaircN) \text{ spectra}M \text{ channel}N$$ (Equation 3)

Figure 6:
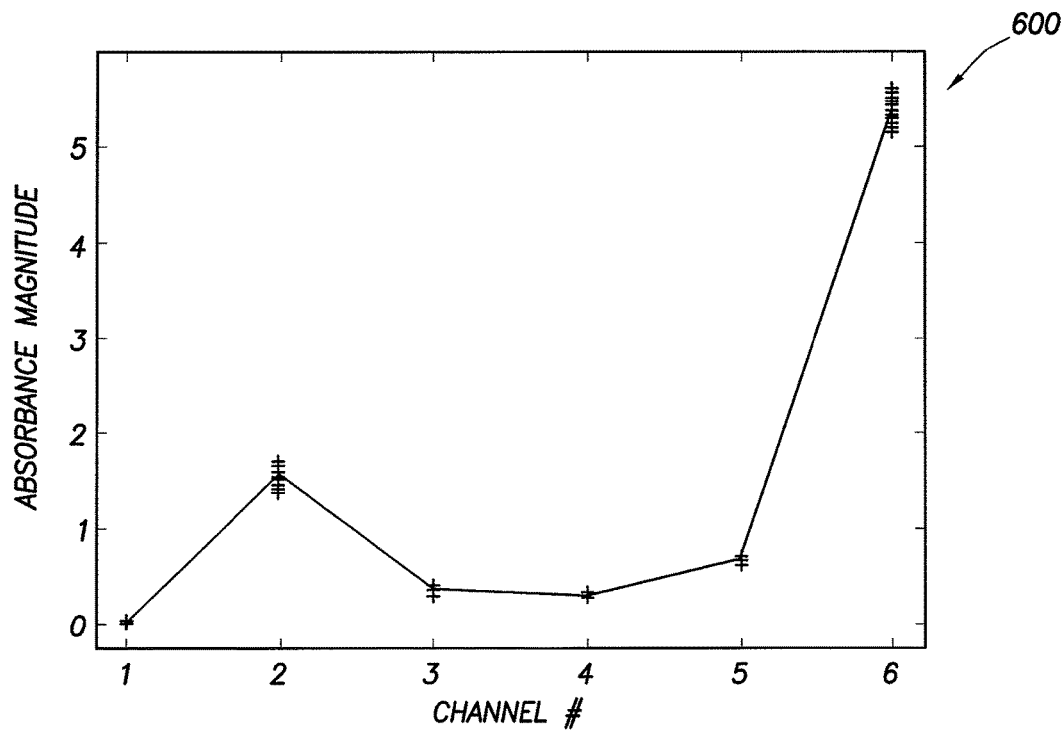
FIG. 6 is an example graph of exemplary theory channel data (absorbance spectra) obtained by transferring database spectra for a spectrometer, in accordance with certain embodiments of the present disclosure.

One of the interference filters from 1500-1600 nm, for example, may be considered as baseline for normalization, although other appropriate baseline regions may be used. FIG. 6 is an example graph 600 of exemplary theory channel data (absorbance spectra) obtained by transferring database spectra for a spectrometer.

Noise and other environmental effects may be added to the theoretical data to appropriately weight the channels according to noise for a particular sensor to translate the calibration function. Adjustments may be made for thermal response in width, peak response, and center wavelength. The dot product of a filter transmission function may then be taken with respect to a secondary instrument I0 function and the instrument translated optimal standard sample set. The absorbance may then be computed from the theoretical or measured filter transmission functions. Instrument equivalent noise may be added to the individual theoretical filter responses to "ruggedize" the calibration with respect to field conditions.

Partial least squares (PLS) regression may be employed as part of the filter set development. However, it should be understood that other appropriate regression algorithms may be used. A calibration coefficient (i.e., GOR) may be developed by PLS regression (b). Table 1, below, provides exemplary GOR calibration coefficient data of North Sea oil by PLS regression.

TABLE 1

GOR calibration coefficient of North Sea oil by PLS regression.

| Channel 1 | Channel 2 | Channel 3 | Channel 4 | Channel 5 | Channel 6 |
|---|---|---|---|---|---|
| baseline | b1 | b2 | b3 | b4 | b5 |

Figure 7:
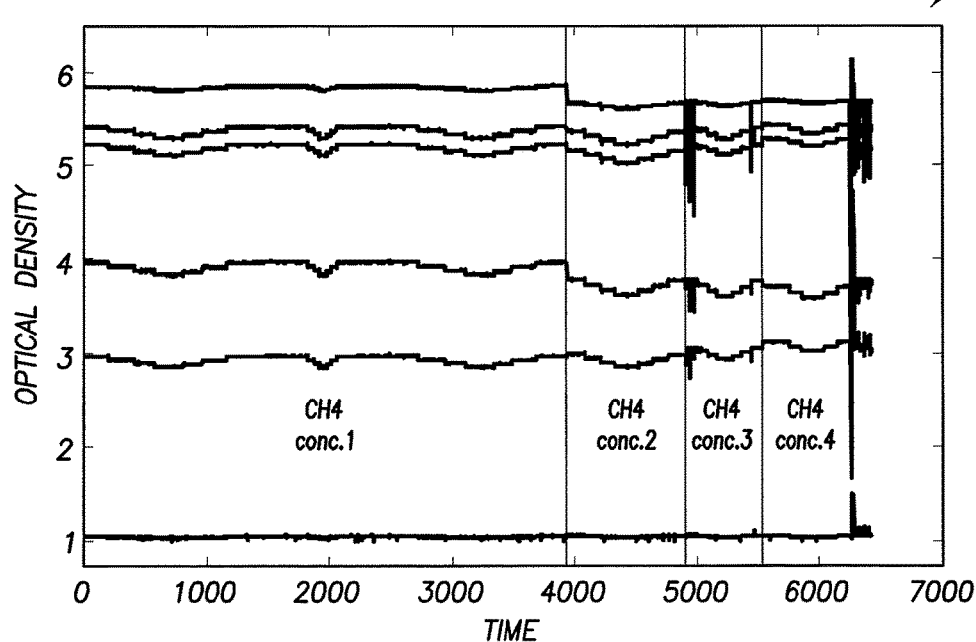
FIG. 7 is an example graph of exemplary filter data of example oil by a spectrometer, in accordance with certain embodiments of the present disclosure.

Real tool data may be collected by the spectrometer, with real noise and environmental characteristics. FIG. 7 is an example graph 700 of exemplary filter data of the same North Sea oil by the spectrometer at 250° F., at 3,000 psi, 6,000 psi, 9,000 psi, 12,000 psi, and at four different CH4 concentrations.

Optical density data may be calculated by taking a negative common logarithm of real tool data. The predicted GOR may be given by:

$$\text{predicted GOR} = (b1*(\text{absorbance data channel2}) + b2*(\text{absorbance data channel3}) + b3*(\text{absorbance data channel4}) + b4*(\text{absorbance data channel5}) + b5*(\text{absorbance data channel6}))$$ (Equation 4)

Figure 8:
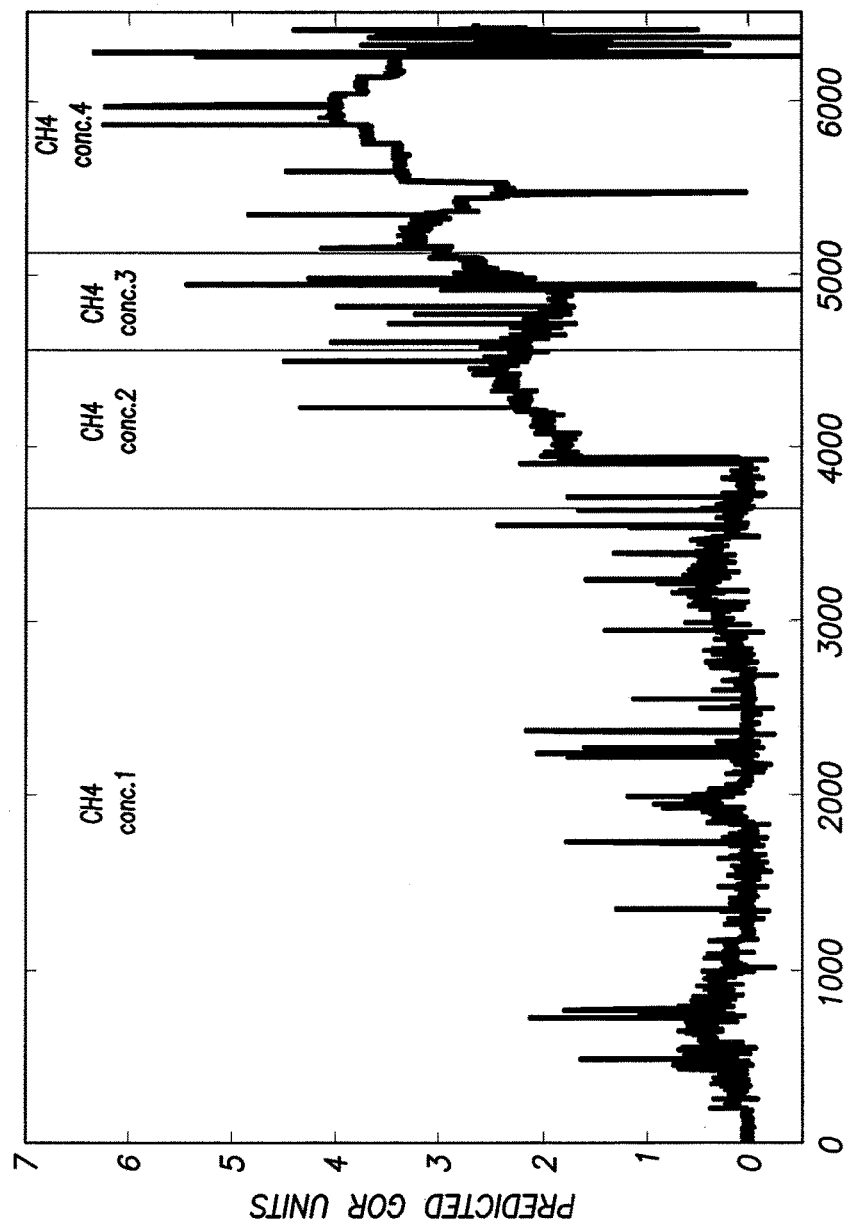
FIG. 8 is an example graph of exemplary predicted GOR (gas/oil ratio) of example oil by a spectrometer, in accordance with certain embodiments of the present disclosure.

FIG. 8 is an example graph 800 of exemplary predicted GOR of North Sea oil by the spectrometer. In the example illustrated in FIG. 8, the noise level is 13 GOR units, precision is 55 GOR units, and accuracy is 73 GOR units for this oil, filter set, and tool configuration.

In some exemplary embodiments, samples that are similar to those which will be analyzed using the tool may be selected to make the prediction more accurate. Often, it is assumed that samples of close geographic location (i.e., from the same field or same basin) would be a set of the optimal samples from which to form a calibration for an unknown sample. Although this may be true, samples from a field or basin may in fact have very different genetic or geological histories. Likewise, samples from the field or basin may simply not be available. Therefore, it may become necessary to select samples from a larger database that most closely represent the "unknown sample." To effectively use the database and facilitate calibration data selection, the samples in the database with diverse patterns may be separated into a number of subgroups (clusters) through clustering, such that the similarity of samples within a cluster is larger than the similarity of samples belonging to different clusters. Raw optical measurements, as well as other physical and chemical measurements (i.e., density, bubble point, capacitance, etc.) may provide a basis for database clustering and classifying new samples with some unknown characteristics.

Clustering algorithms may be based on diverse principles such as distance and similarity measures, hierarchical and graph theory, squared error, combinatorial search, neural networks, fuzzy inference, and/or SIMCA (Soft Independent Modeling of Class Analogy). Although there may be no clustering algorithm that can be universally used to solve all problems, some algorithms are better than others for the given applications. Since an optical fluid database may have extra-high dimensionality, one or more clustering algorithms suitable to a large-scale data set may have to be selected.

The following non-limiting example shows how neural network based clustering may be used to construct a self-organized feature map (SOFM) applied to raw optical measurements at selected channels. A SOFM algorithm may utilize a competitive neural network to initialize and update a number of neuron weighting vectors corresponding to a centroid of each cluster. A determination of the weighting vectors may be achieved through iterative training to minimize a distance of one or more member samples to a centroid neuron. In classification, a new sample may fill in a certain cluster if its input vector has the nearest distance to that neuron. The winner neuron (cluster) may output 1 while other neurons output 0.

Figure 9A:
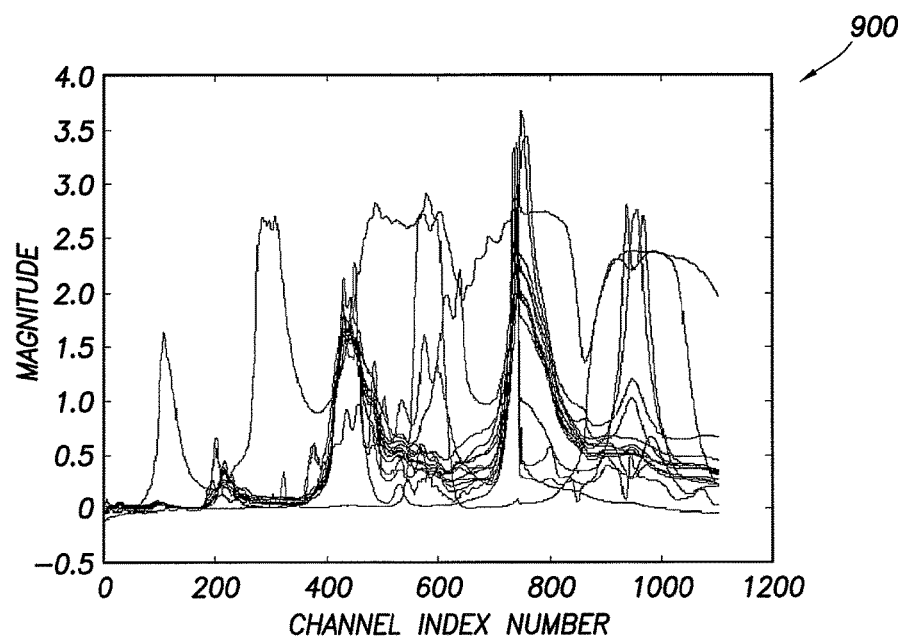
FIGS. 9A through 9H are graphical representations of a non-limiting example of SOFM (self-organized feature map) clustering applied to an optical fluid spectrum, in accordance with certain embodiments of the present disclosure.
Figure 9B:
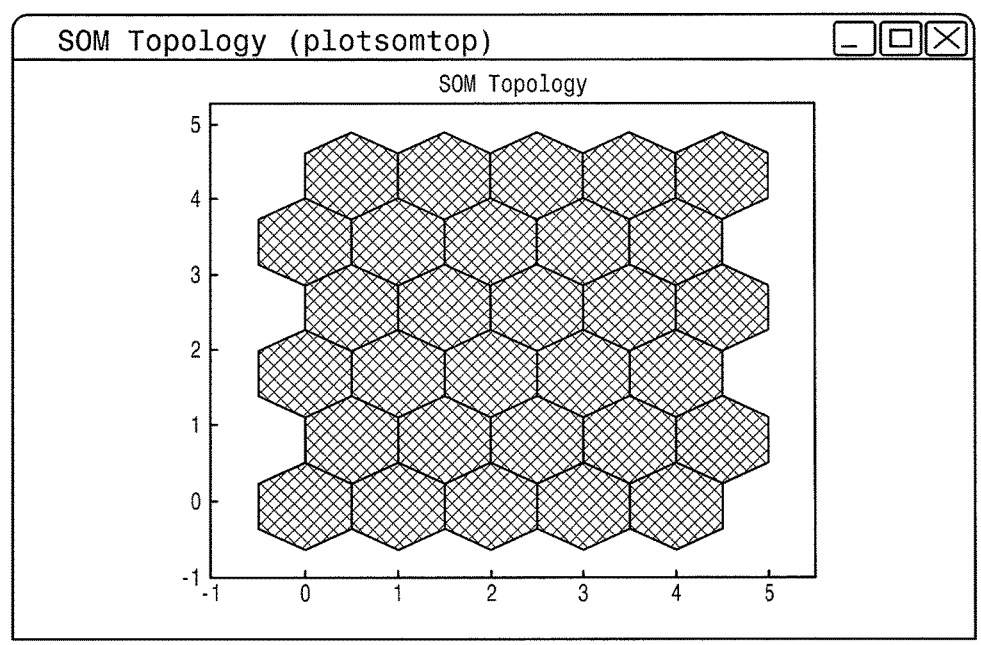
Figure 9C:
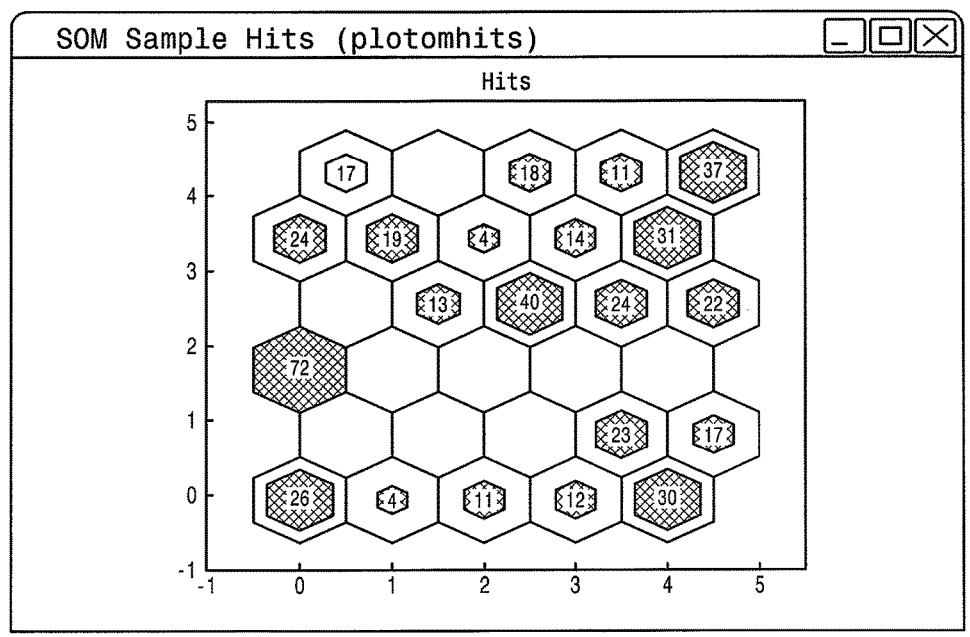
Figure 9D:
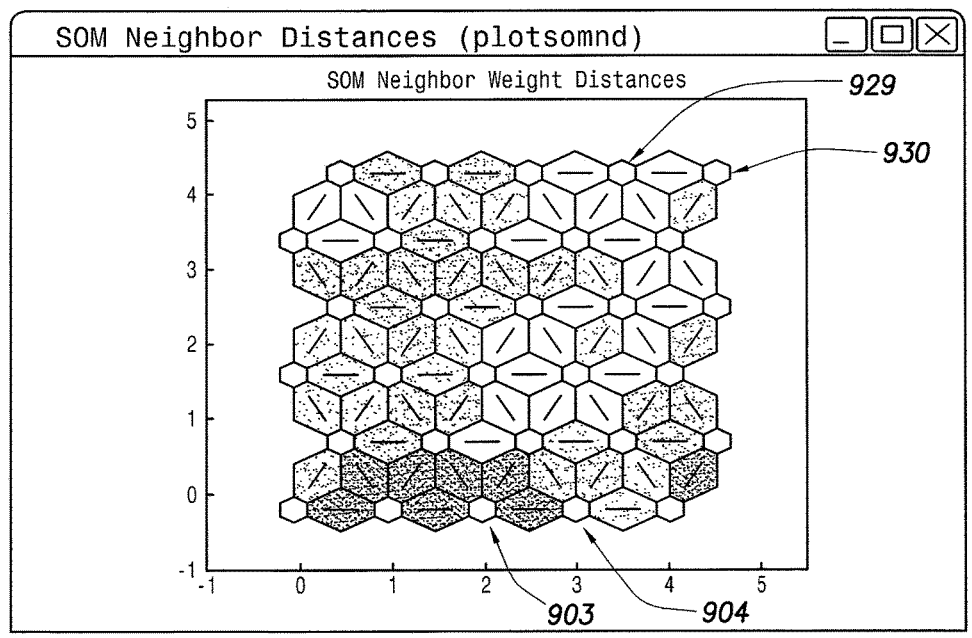
Figure 9E:
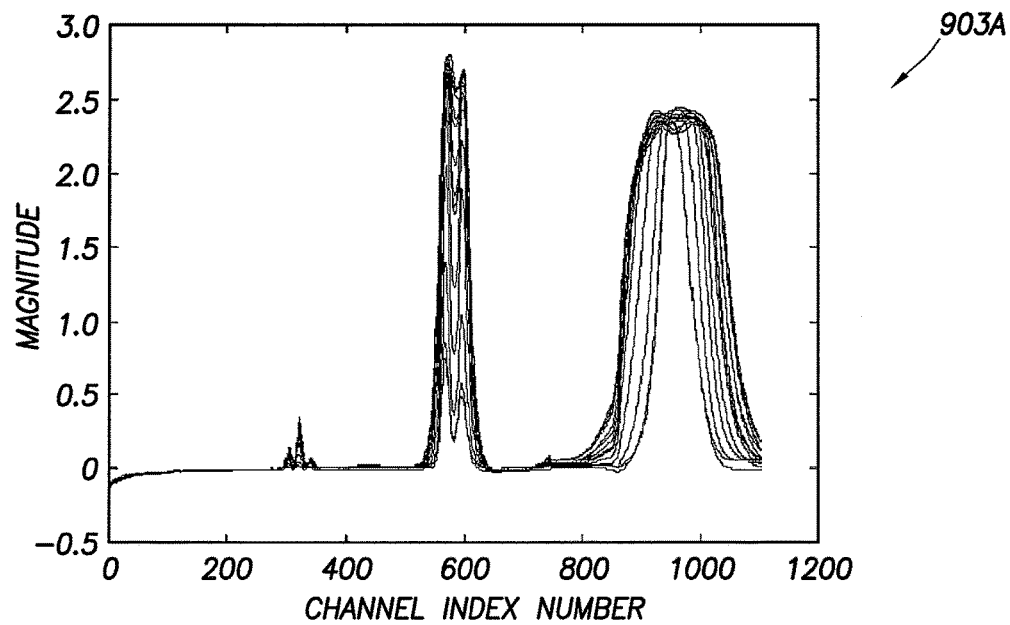
Figure 9F:
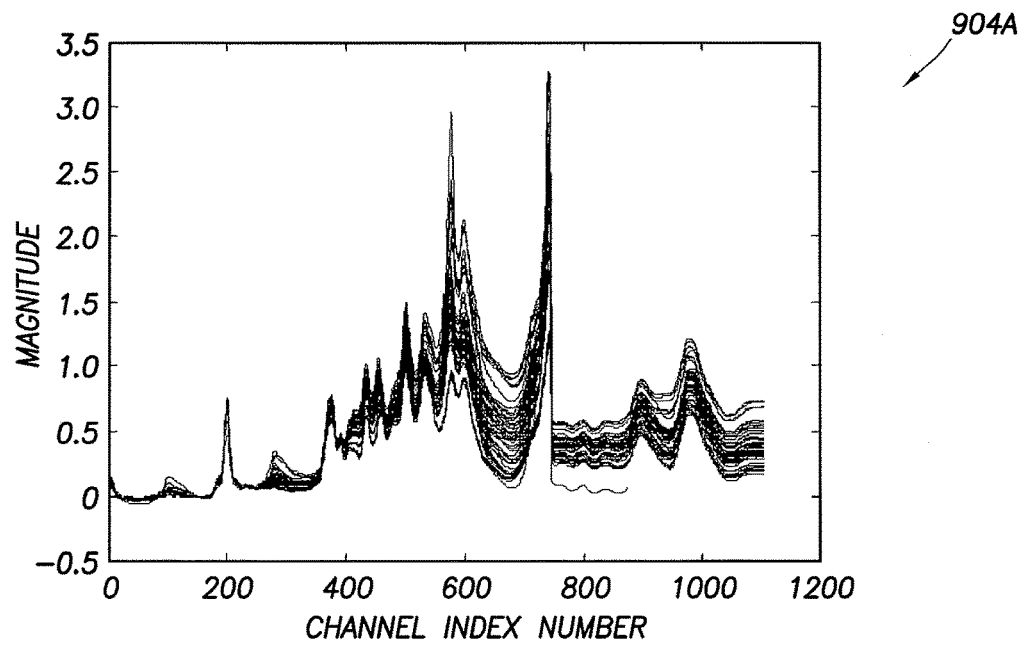
Figure 9G:
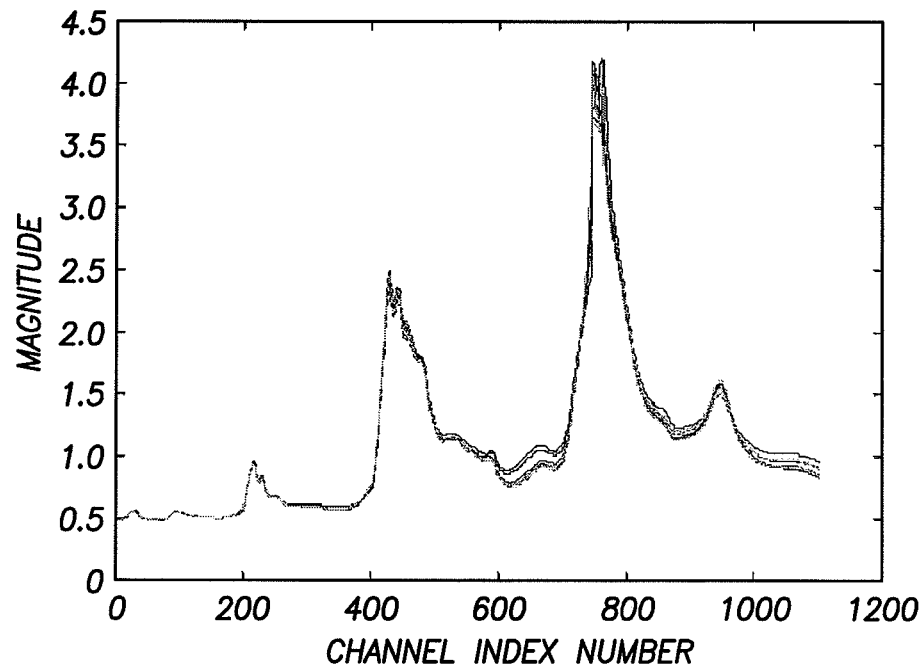
Figure 9H:
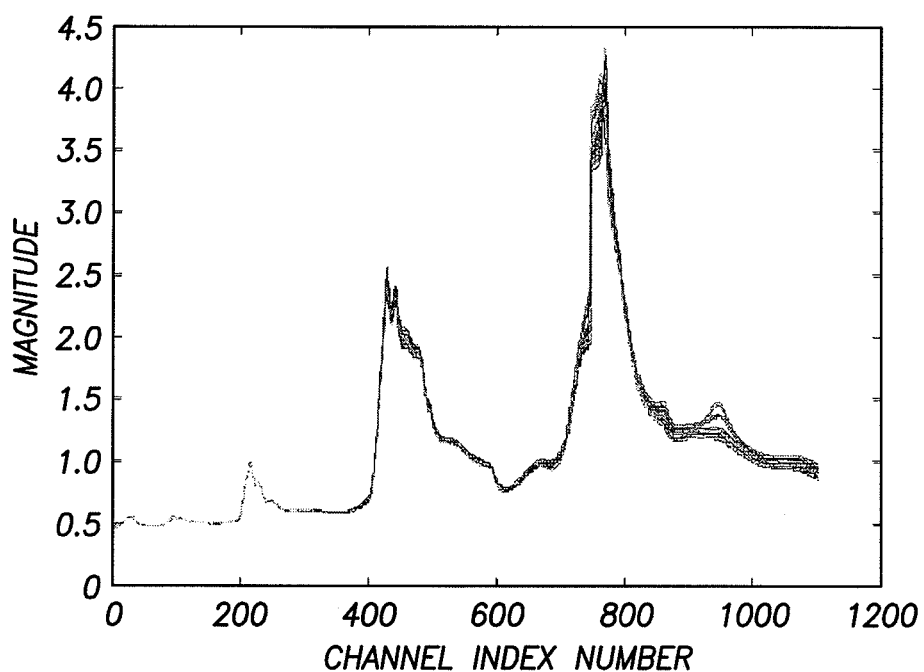

FIGS. 9A through 9H are graphical representations of a non-limiting example of SOFM clustering applied to an optical fluid spectrum, in accordance with certain embodiments of the present disclosure. The spectrum 900 in the non-limiting example of FIG. 9A includes 469 samples from a small database of formation fluids at a selected channel, with some spectra in FIG. 9A moved for clarification. In FIG. 9B, 30 clusters are initiated for a SOM (self-organizing map) topology. FIG. 9C shows actual hits of samples on each cluster after competitive network training. Some weight vectors of neurons attract a large number of samples. Some others are not activated after initialization. At the end of training, only 21 clusters are filled with samples. FIG. 9D illustrates SOM neighbor weight distance. Specifically, FIG. 9D shows 30 nodes in total, representing 30 initiated clusters. In one exemplary embodiment, the cluster number may be assigned from bottom left to top right, from 1 to 30, as shown in FIG. 9D. The connections of clusters are shaded from darker (corresponding to being further apart) to lighter (corresponding to being closer together) to show how close each neuron's weight vector is to its neighbors. In FIG. 9D, the clusters 3 and 4 are respectively indicated as 903 and 904. As shown in FIG. 9C, the clusters 3 and 4 are respectively filled with 11 and 12 samples. In FIG. 9D, the clusters 3 (903) and 4 (904) are shown with longer distance between weight vectors that have totally different spectrum profiles and are connection coded with darkest shading. The sample profiles 903A and 904A of these two clusters are shown in FIGS. 9E and 9F, respectively. In FIG. 9D, the clusters 29 and 30 are respectively indicated as 929 and 930. In FIG. 9C, the clusters 29 and 30 are filled with 11 and 37 samples, respectively. In FIG. 9D, the clusters 29 and 30 are connection coded with lightest shading to indicate close similarity with shorter distance between weight vectors. The similar sample profiles 929A and 930A of these two clusters are illustrated in FIGS. 9G and 9H, respectively.

In practice, once spectra of field fluid samples are obtained, the procedure of pattern identification/reorganization may be applied first to classify the samples into corresponding nearest clusters in the database. Then, the samples from these clusters may be used to construct a calibration model. Using SOFM, the ordinal clusters may be found as needed to satisfy the requirements of calibration transfer if adequate fluid samples in types and environmental variations exist in database.

Accordingly, pattern classification/recognition may be applied to the high-dimensional spectrum database. Similarly, pattern classification/recognition may be applied to the dimension-reduced database after the genetic algorithm incorporated channel selection and/or other pre-processing (principal component analysis, for example) are performed. Since the final calibration model may be based on the reduced inputs, it may be advantageous to check the clustering agreement and see if any unexpected information loss is exhibited due to dimensionality reduction, or if additional samples need to be selected from database to ensure adequate information in building the calibration model.

Although data can be missing from the database for any specific samples, one or more of the following methods may be used to classify with missing data: multiple imputations; Markov chain Monte Carlo simulation; maximum likelihood estimation (EM algorithm); and Bayesian inference. Multiple imputation is a technique in which each missing value is replaced by m simulated values where m>1. The m sets of imputations may be created to reconstruct m plausible versions of the complete data, each of which may be analyzed by standard complete-data methods. The results of the m analyses may be combined to produce a single inferential statement (e.g., a confidence interval or a p-value) that includes uncertainty due to missing data.

In certain embodiments, the simulated values may be generated by using techniques of Markov chain Monte Carlo, EM algorithm (maximum-likelihood estimate), and Bayesian inference. The EM algorithm is a general technique for finding maximum-likelihood estimates for parametric models when the data points are not fully observed. The Markov chain Monte Carlo is a body of methods for generating pseudorandom draws from probability distributions via Markov chains. A Markov chain Monte Carlo is a sequence of random variables in which the distribution of each element depends on the value of a previous one. In Bayesian inference, information about unknown parameters is expressed in the form of posterior probability distribution. Through Markov chain Monte Carlo, it is now possible in many cases to simulate the entire joint posterior distribution of the unknown quantities, and thereby obtain simulation-based estimates of virtually any features of the posterior that are of interest. Additionally, extrapolated properties for missing data generated via MATLAB®'s ALSPCA package can be used.

In addition to reconstructing a complete data set via multiple imputation, an analytical database may also be built with various clustering results included using variable dimensionality. For example, if complete data dimensionality is 10, data patterns may be constructed through clustering analysis by using full and reduced variables, respectively. Once certain parameters are missing from samples, one may find a partially fitting cluster using remaining parameters.

This may narrow the range for parameter selection with the use of multiple imputations and may facilitate training data selection for calibration model development.

The problem with missing data may be aggravated with the problem of inconsistent data, especially when the sample measurements used for database construction come from different labs. The measurement inconsistencies could be system and procedure dependent, and empirical equations for system compensation of different data sources may need to be established. Dealing with inconsistent data may also take an approach similar to dealing with missing data via multiple imputations. Thus, the techniques described herein may be used to normalize data from different laboratories and different instruments.

Figure 10:
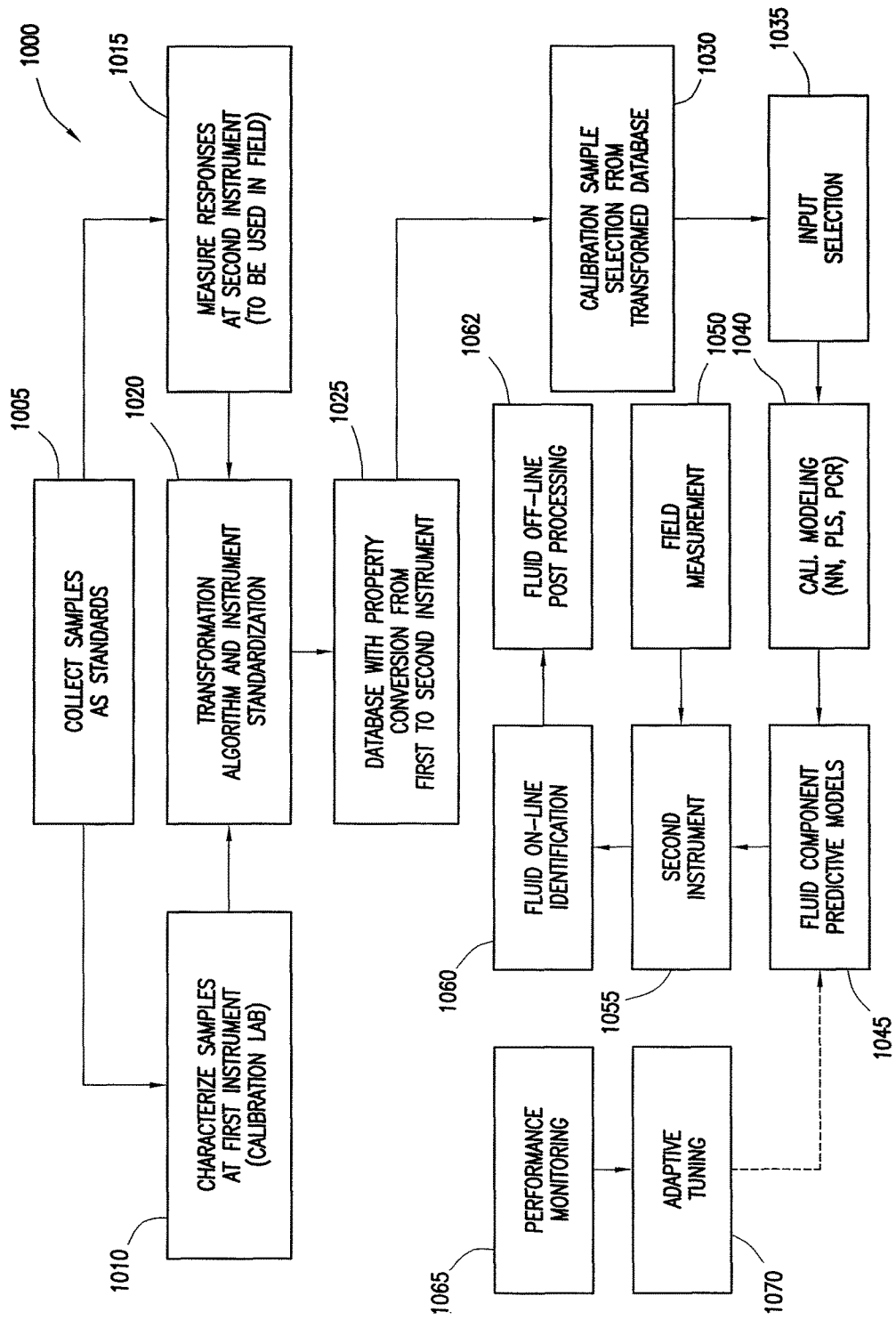
FIG. 10 is a flowchart illustrating one example method of calibration transfer from a library to an individual tool, in accordance with an exemplary embodiment of the present disclosure.

FIG. 10 is a flowchart illustrating one example method 1000 of calibration transfer from a library to an individual tool, in accordance with an exemplary embodiment of the present disclosure. Teachings of the present disclosure may be implemented in a variety of ways. As such, the steps comprising method 1000 and the order of those steps may depend on the implementation chosen.

According to one embodiment, method 1000 may begin, as indicated by block 1005, with collecting samples to serve as standards. The standards may be representative of the "universe" of samples to be analyzed. By way of example, without limitation, one or more samples from a global oil library may be used as standards. Other samples which are not in the set of characterized fluids, or even oils, could be used so long as they have "lever arm" sensor responses. Materials having lever arm sensor responses may not be hydrocarbons, but may have inordinately large responses that provide a full scale or a near-full scale response. Materials having lever arm sensor responses may have a response that sufficiently mimics methane for calibration or actually hyper-mimics methane and it may be both safer and less volatile in the field. As a non-limiting example, a phenolic may provide the ability to use a thin sheet of the material and obtain a response that may be two or three times the benzene content expected in an oil. In certain embodiments, the material thickness may be manipulated to manipulate the proportional response. Thus, the materials may be used as solid standards. Lever arm samples provide the greatest calibration transfer capability ranked from most influential to least influential according to the inherent dimensionality with respect to the calibration, and they need not be fluids but can be optical elements with proper optical responses. The lever arm samples may be selected as standards according to the response of the sensors which do not strictly match the characteristics of the normal analyte samples. For instance, lever arm samples may include one or more of water, acetone, ethyl alcohol, silicone oil, and hexane.

As indicated by block 1010, one or more samples may be characterized at a first instrument. Standard samples may be analyzed with respect to properties of interest to be determined. In certain embodiments, the sample characterization may be performed at a calibration lab. Sample characterization for oil may include determining one or more classification properties including, but not limited to, GOR, methane (CH4) concentration, and SARA properties. The standard samples may be analyzed with respect to one or more deterministic responses/properties—e.g., optical density at characteristic wavelengths. Sample characterization may include determining one or more tool response properties across the filter instrument. Lever arm standards may be designed to give strong artificial responses to properties and therefore weight the calibration transfer. The standard samples may be analyzed with respect to optimal classification properties. Some of these properties may be the same as or inclusive of the properties/responses above. Optimal classification properties may be characterized by the ability to classify, as well as the ease of implementation. For example, a gas chromatogram may be very good for classification but not applicable downhole, whereas optical density, although not as good as a chromatogram for classification, may actually be optimal because it is sufficient for classification and easily implementable.

Classification properties, deterministic properties, and response properties may be converted into a transformed database for the second instrument. As indicated by block 1015, responses to the collected samples may be measured at a second instrument to be used in the field. The same samples may be scanned at the second instrument to determine tool response. It should be noted that sections of the optical train may be characterized, as opposed to the whole system. For instance, "designer elements" may be used in the sample cell position for the main tune, and the cell may be characterized separately. The filter wheel can also be characterized on a test fixture as an optical element.

As indicated by block 1020, a transformation algorithm may be developed or identified for instrument standardization as between the first instrument and the second instrument. In certain embodiments, the transformation algorithm may be tested, and block 1015 may be iterated until sufficient test results are achieved. Then, the database corresponding to the standard samples may be converted for the second instrument based on the transformation algorithm.

The transformation algorithm and instrument standardization may be implemented in different ways. In certain embodiments, the spectra from one instrument may be adjusted to look like spectra from the other instrument by using either a linear or a non-linear method. For instruments of the same type, a transformation matrix may need to be developed for a linear approach, and the techniques called Direct Standardization (DS) and Piecewise Direct Standardization (PDS) may be applied for constructing transformation matrices in certain embodiments. In certain embodiments, a non-linear approach with a neural network transformation algorithm, for example, may be suitable to filter an instrument due to its significantly reduced dimensionality of the optical response and enhanced nonlinearity associated with interaction of filter manufacturing tolerance, operating temperature, and jitter effect, etc. with spectra. In certain embodiments, a traditional approach using a fully connected feed-forward neural network trained with back-propagation may be used for such an application to overcome the problem of over-fitting. In certain embodiments, an arbitrarily connected neuron structure trained with feed-forward calculation only may be used and may lead to reduced number of coefficients in transformation algorithm and improved generalization. In addition to neural networks, other non-linear regression and mapping methods such as support vector machine (SVM) and radial basis function with optical inputs may be used.

As indicated by block 1025, in certain embodiments, selected sample properties or spectra of interest measured on the first instrument may be converted to a transformed database for the second instrument before use, through a single (universal) or multiple transformation algorithms developed during instrument standardization. Alternative approaches for spectra adjustment using transformation algorithms may apply if only minor differences between the first and the second instrument are exhibited. Therefore, a predictive calibration model may be built directly based on the first instrument. The calibration may then be adjusted when the data from the second instrument is available. Depending on the nature of the instrument, robust calibration may be made without transformation, which allows combining the spectra collected from the tools to form a hybrid database for future predictive modeling. In such a case, the property conversion of the standard samples from first instrument to the transformed database for the second instrument, indicated by block 1025, may be omitted, which may provide convenience for some applications.

As indicated with block 1030, a calibration training sample selection from the transformed database may be performed. Classification properties of an unknown sample to be determined may be measured via the second instrument, and the unknown sample obtained may be projected against the classification system. Samples used to build a calibration model for unknown sample property prediction are selected from the transformed database. A calibration training sample selection may ensure that the samples are close and the unknown samples are bracketed in classification space and have a sufficient analytical "lever arm" of calibration. Accordingly, optimal standard samples for training set characterization may be selected from the transformed database, may be close to the unknown sample in classification space, may bracket the unknown sample in classification space, and may have a sufficient analytical "lever arm" of calibration.

Vectors of existing calibration may be rotated mathematically, or a new subset calibration may be created for the unknown sample. The unknown sample may be projected against the calibration scheme for deterministic properties. The sample may be added to a local database for nearest neighbor classification within a field (i.e., is the next time series sample the same as the last, close to the last, or far from the last in the classification space). Samples may be classified in a global context. With enough field samples, new field samples may be classified against themselves. With even more field samples, the field samples may be divided into subclasses for clustering. Sample selection may involve using appropriate clustering algorithms, such as Self Organized Feature Map (SOFM) and Hierarchical Clustering (HC), that can be applied to full spectra, filtered spectra, transformed spectra (FFT and wavelet, for example) and other classification properties.

After clustering-based preliminary sample selection is performed, the refinement of selection may be followed using a backward stepwise routine and incorporated with model input selection corresponding to block 1035. The need for model input selection corresponding to block 1035 may be justified from several points of view. Even with a filter instrument, for example, the further input selection for single output model development is necessary, since the full filter set (which may be more than 10 filters, for example) inputs, which are applied to multi-component prediction for fast simulation with GA at stage of design, might be redundant in applications with single output prediction. In certain embodiments, a backward stepwise input selection algorithm may be implemented which may be used to remove the least significant input each time for linear and non-linear model comparison in determining the best set of calibration inputs. The algorithm may also be applied to training sample selection by removing a least relevant fluid sample from the calibration data each time to minimize the prediction error on validation of a sample property which might be a good representative of the property of unknown new samples.

Figure 11:
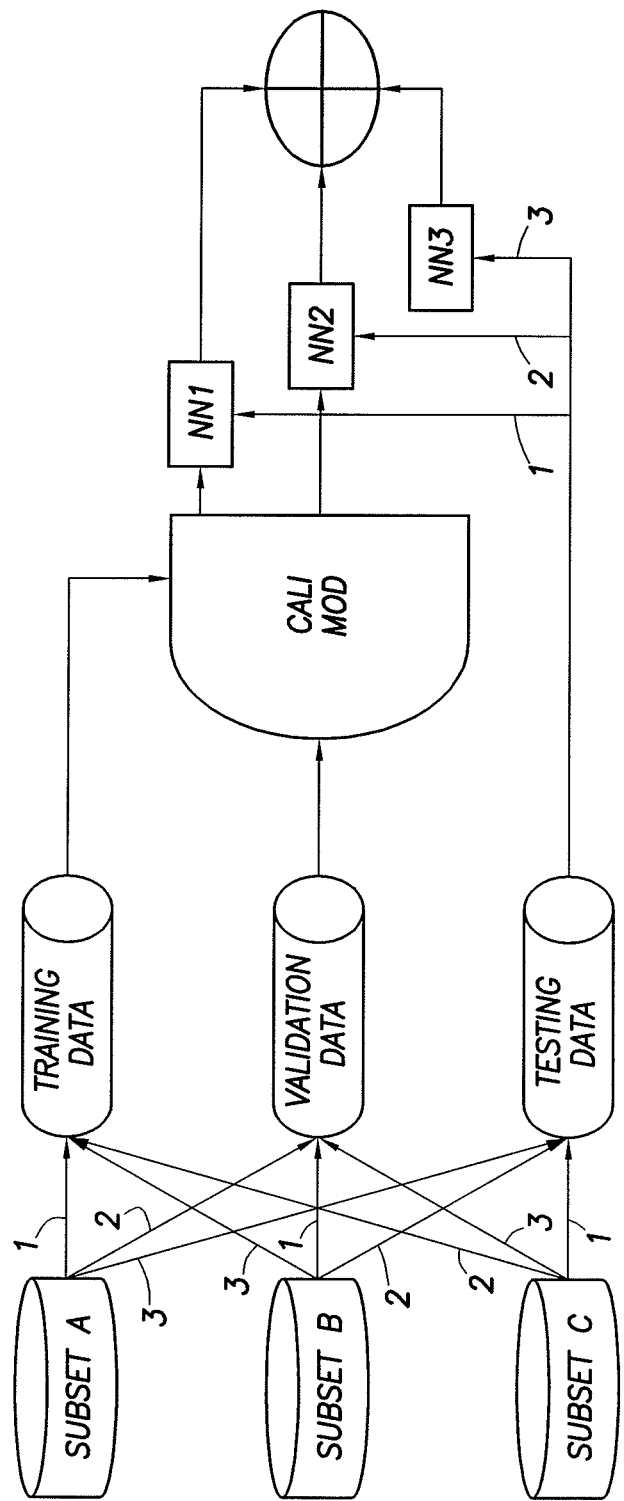
FIG. 11 illustrates a process of calibration modeling with multiple neural networks, in accordance with certain embodiments of the present disclosure.

FIG. 11 illustrates a general process of calibration modeling with multiple neural networks, in accordance with certain embodiments of the present disclosure. The general approach depicted corresponds to the calibration modeling indicated by block 1040, according to certain embodiments, using either neural network, or PLS/PCR (partial least squares/principal component regression) or a combination of some of the above. The data used for calibration may be divided into training, validation and testing sets to build several neural network models. In certain embodiments, the calibration data may be randomly divided into several disjointed subsets. The training set may be directly applied to model parameter optimization, and its performance function may be monotonically improved with increase of training epochs or iterations. The validation set may accompany the training set and may be used to terminate the training at the right time when validation error reaches its minimum. The testing set may allow testing of the model performance after the training is done.

In the non-limiting model fusion example depicted, a first neural network model (NN1), a second neural network model (NN2), and a third neural network model (NN3) are depicted. A subset A may be used as a training set for NN1, as a validation set for NN2, and as a testing set for NN3. A subset B may be used as a validation set for NN1, as a testing set for NN2, and as a training set for NN3. A subset C may be used as a testing set for NN1, as a training set for NN2, and as a validation set for NN3. The testing set applied to NN1 may be subset C; the testing set applied to NN2 may be subset B; and the testing set applied to NN3 may be subset A. A testing error can be summed or averaged over three networks for overall performance evaluation. Because NN (neural network) performance is affected by parameter (connection coefficients) initialization, model structure and training algorithm, multiple runs might be needed during the calibration modeling in determining the best member networks for model fusion. The process illustrated in FIG. 11 may be implemented as a primary routine for NN calibration modeling. The best three networks determined in this way may be uploaded to the second instrument for on-line application, as indicated by blocks 1055 and 1060 in FIG. 10.

Figure 12:
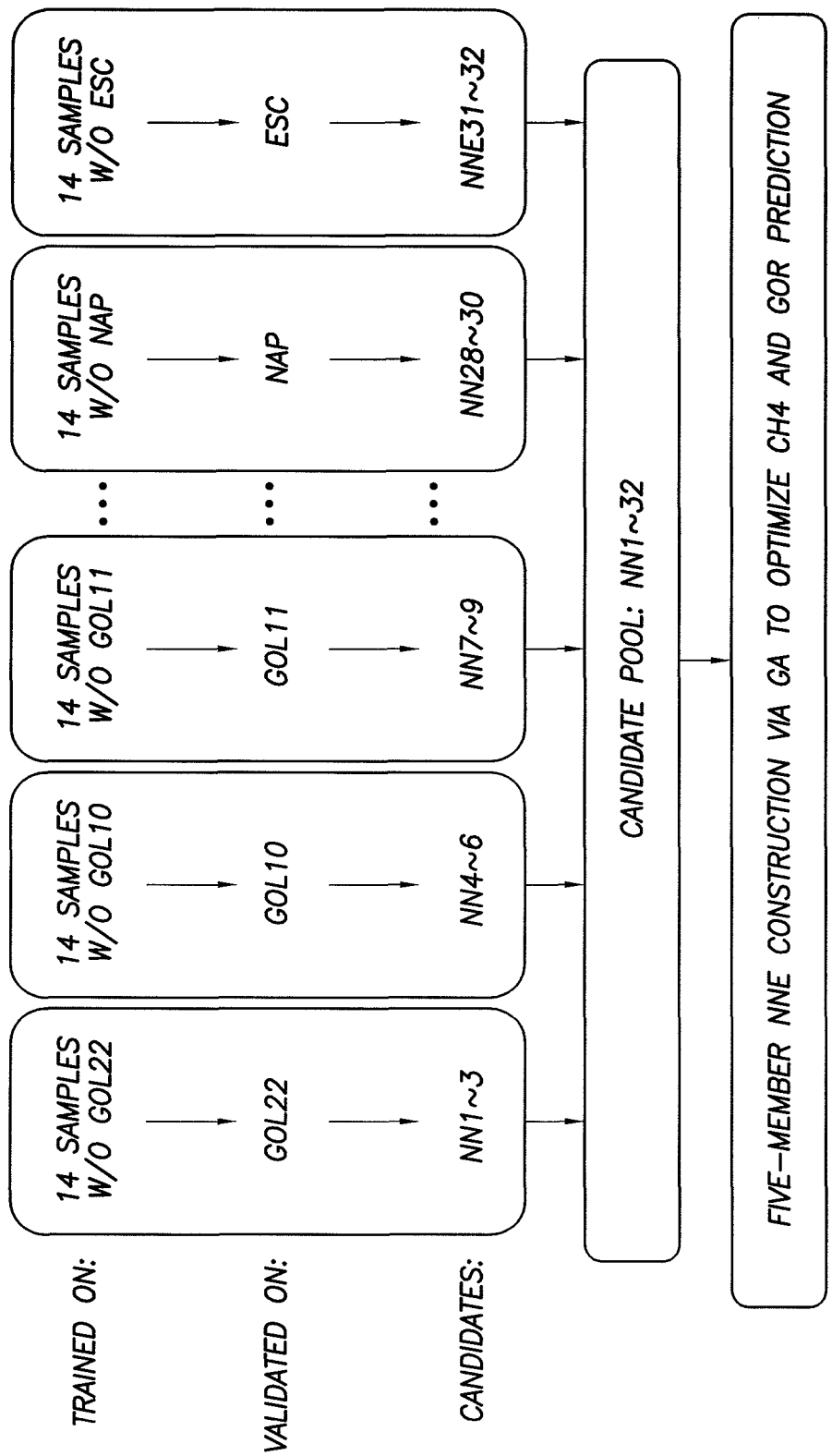
FIG. 12 illustrates a five-member neural network ensemble or committee approach, in accordance with certain embodiments of the present disclosure.

A fluid component predictive model indicated with block 1045 may be a single model realization, a model ensemble or fusion. FIG. 12 illustrates an exemplary optional approach, in accordance with certain embodiments of the present disclosure. In FIG. 11, the three generated networks are respectively tested on the different sets of data to form a final model. In FIG. 12, a five-member NN ensemble or committee may be selected from a model base (candidate pool) which is constructed with a more complicated calibration routine. Some candidate networks (NN1-3, for example) may be trained on some samples and tested on a particular sample (GOL22, for example). The other candidates (NN4-6, for example) may be trained on different channel inputs and data and tested on another sample (GOL10, for example). The model base (not limited to 32 members) may be constructed gradually to retain the continued effort of calibration modeling when new standard samples become available. The selection of the five-member ensemble may be optimized with a genetic algorithm to minimize the prediction error of certain fluid properties (CH4 concentration and GOR, for example) based on all available samples or partial samples if prior knowledge of a fluid type to be measured is available. The five-member ensemble uploaded into the second instrument, as indicated by block 1055 of FIG. 10, may vary for different formation testing jobs. Therefore, ensemble re-selection from model base may be needed with different on-line applications. The model base may also provide convenience for off-line post processing, indicated by block 1062, by using different candidate networks to correct on-line prediction error when the problem of on-line model is identified such as unanticipated fluid type change and channel failure due to damage of particular spectrometer filter(s).

As indicated with blocks 1050, 1055 and 1060, the second instrument, with calibrated predictive model implemented, may take field measurements, and process data to provide real-time fluid identification. As a quality control element, performance monitoring, indicated by block 1065, may be used to check predictions and ensure the output fluid component is in the range of common knowledge of training samples, or within a certain pre-described tolerance. As indicated with block 1070, once the poor prediction is detected, a software routine may be activated to make an adjustment, replace the current predictive model with an alternative model also implemented in the field instrument, or suggest re-calibration as needed.

In the following non-limiting example, sample spectral data—12 fluid samples (with 592 variations) obtained from a optical-PVT system and the simulated filter response—was used to create difference in tool response between a first instrument and a second instrument. Then, instrument standardization was performed by using a neural network transformation algorithm. Local calibration models were built through sample selection and input selection for fluid component prediction. A testing oil sample (99 variations), unseen from calibration transfer, was used to validate both transformation algorithm and calibration models.

Figure 13:
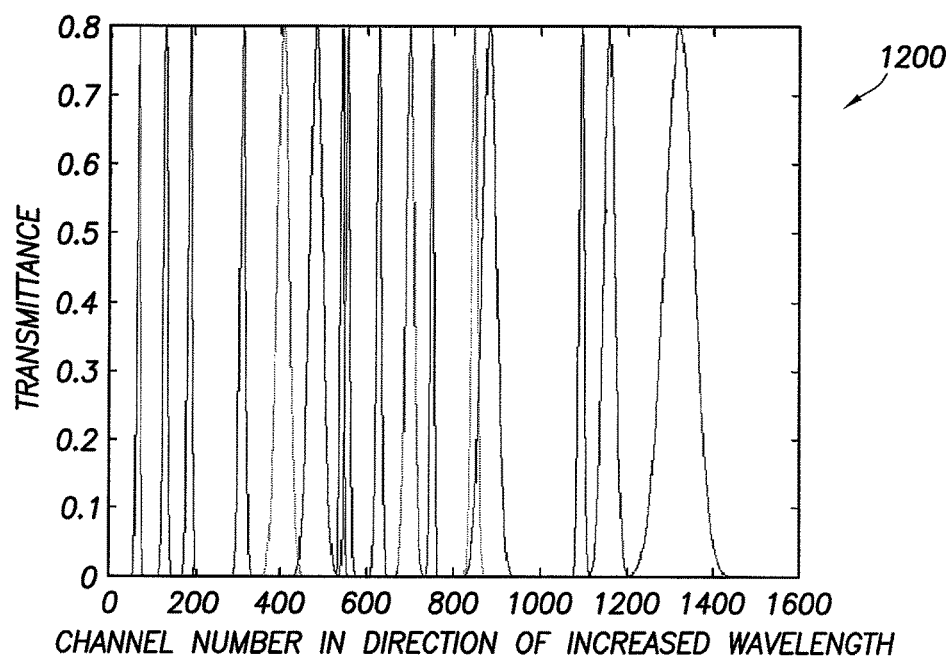
FIG. 13 is a graph of an ideal Gaussian filter set selected for spectrometer design, in accordance with certain embodiments of the present disclosure.

FIG. 13 is a graph 1200 of an ideal Gaussian filter set selected for spectrometer design, in accordance with certain embodiments of the present disclosure. The example of an ideal Gaussian filter set includes 18 member filters selected from GA/PLS simulation, which may be implemented in a spectrometer to obtain an optical tool response in accordance with certain embodiments. Fabricated filters may never have ideal responses. Their center wavelength (CWL) may shift a random amount, and manufacturing tolerance may be a function of CWL. Therefore, actual filter responses may not be the same even with the same design parameters, resulting in one source of variation among the instruments.

Figure 14:
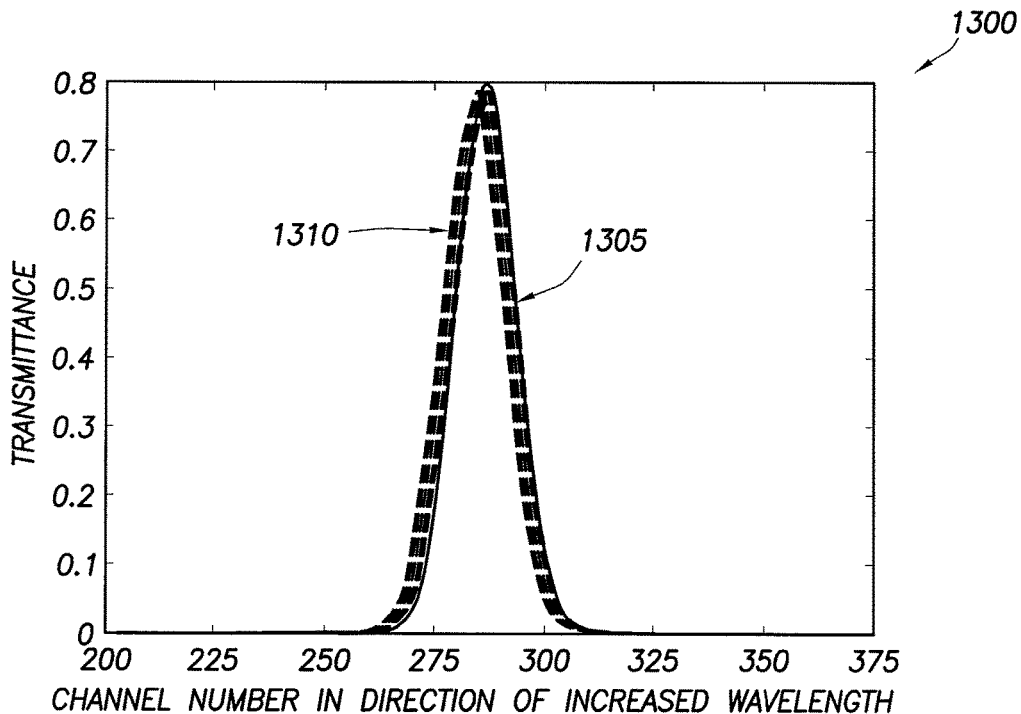
FIG. 14 is a graph 1300 demonstrating the jitter effect on a single Gaussian filter simulated with a special tool configuration, in accordance with certain embodiments of the present disclosure.

More differences may be observed among tools under diverse environmental/operating conditions. FIG. 14 is a graph 1300 demonstrating the jitter effect on a single Gaussian filter simulated with a special tool configuration. The curve 1305 may correspond to an ideal filter. The curve region 1310 shows possible filter responses associated with vibration.

Figure 15:
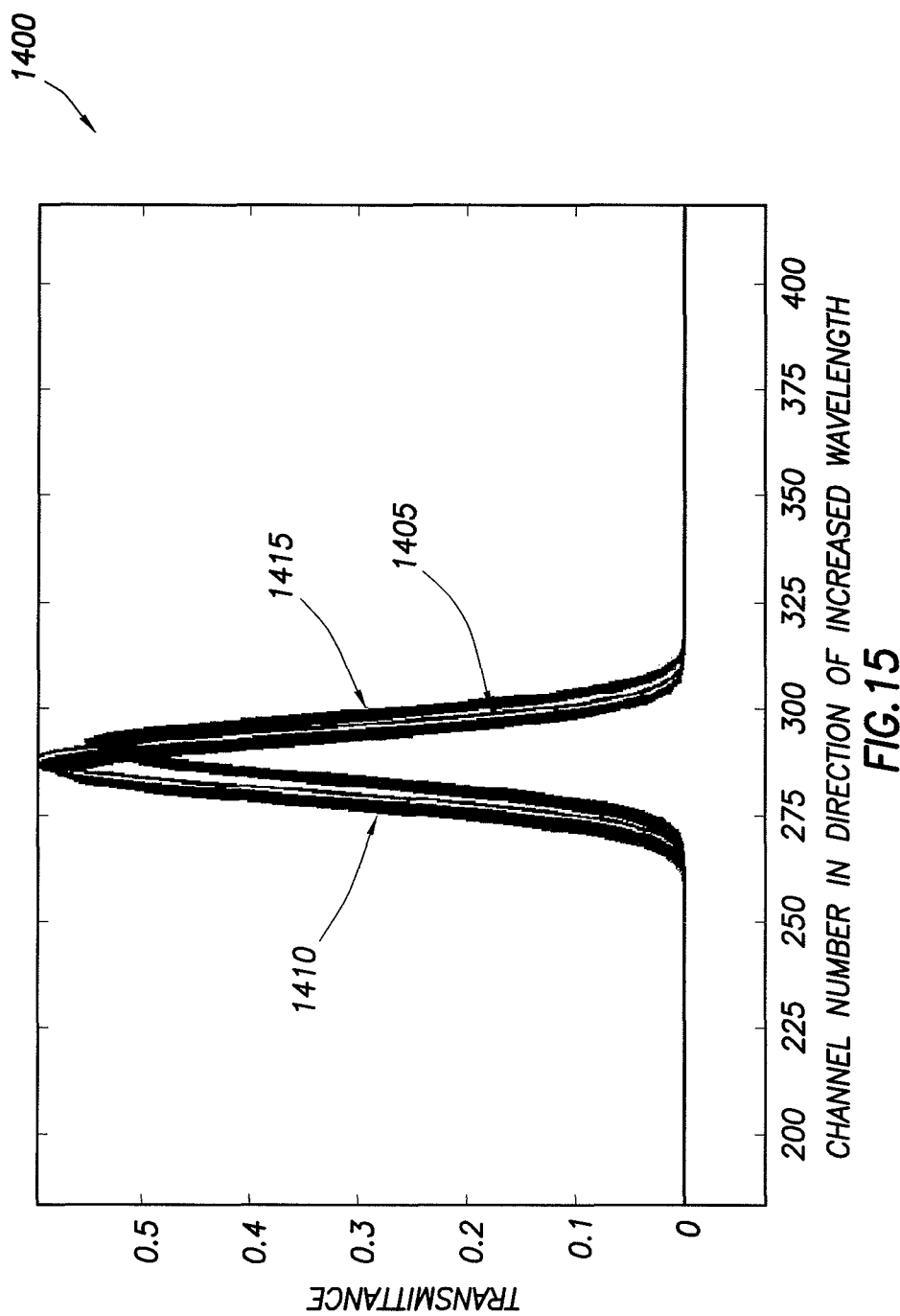
FIG. 15 is a graph of temperature and jitter effect on a single Gaussian filter response, in accordance with certain embodiments of the present disclosure.

FIG. 15 is a graph 1400 of temperature and jitter effect on a single Gaussian filter response. The integrated effect of filter temperature and jitter may cause changes in wavelength, transmittance and bandwidth. The curve 1405 may correspond to an ideal filter. The curves 1410 may correspond to Gaussian filter response under jitter and 65° C. The curves 1415 may correspond to Gaussian filter response under jitter and 175° C. Other influential factors, such as blackbody effect and index of refraction effect, may be combined with temperature and pressure effects to change light source intensity and cell path, leading to the variation in spectra and the consequent tool response.

Figure 16:
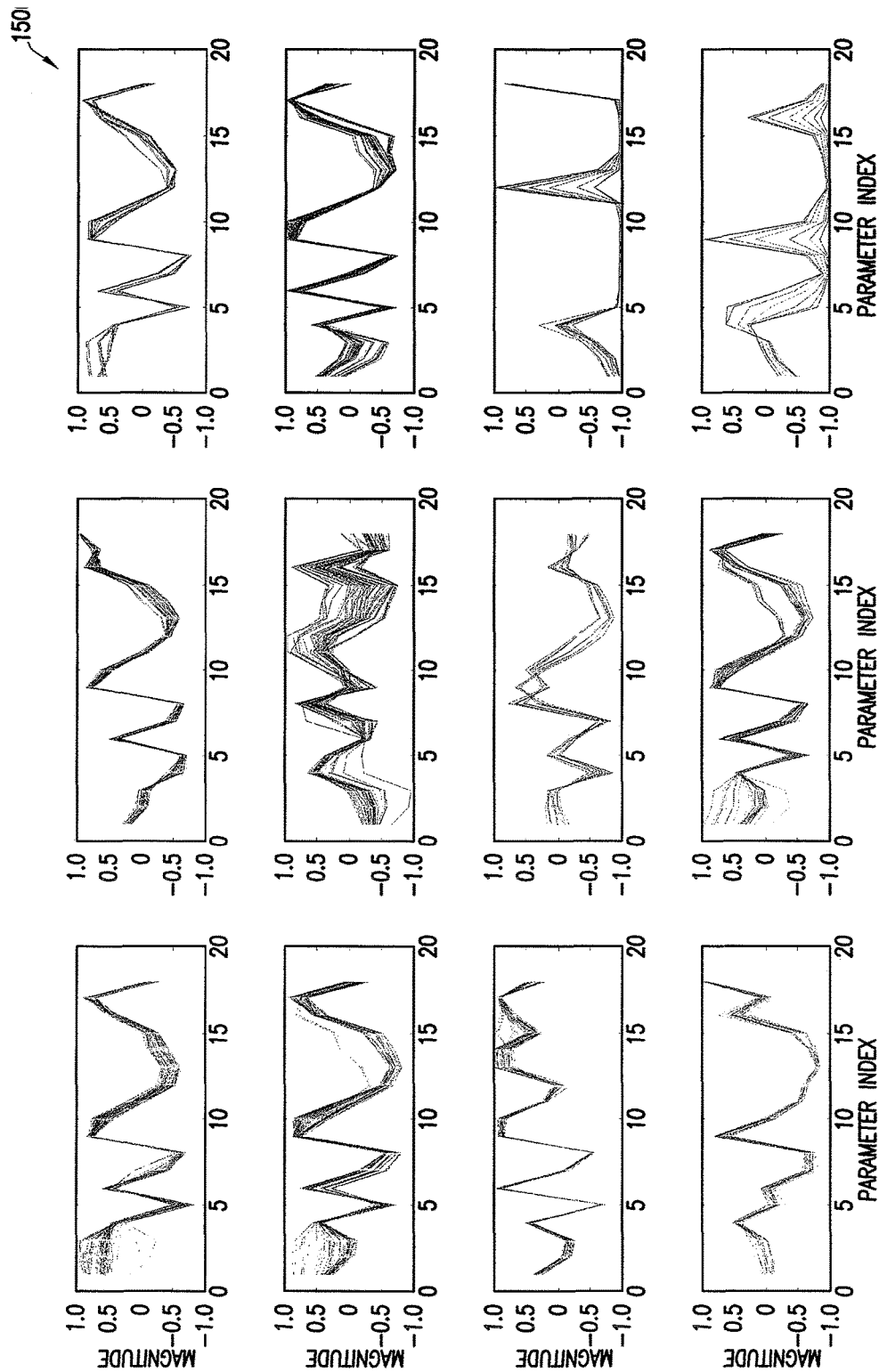
FIG. 16 illustrates a graph set showing a tool response of 12 samples obtained from a first instrument, in accordance with certain embodiments of the present disclosure.
Figure 17:
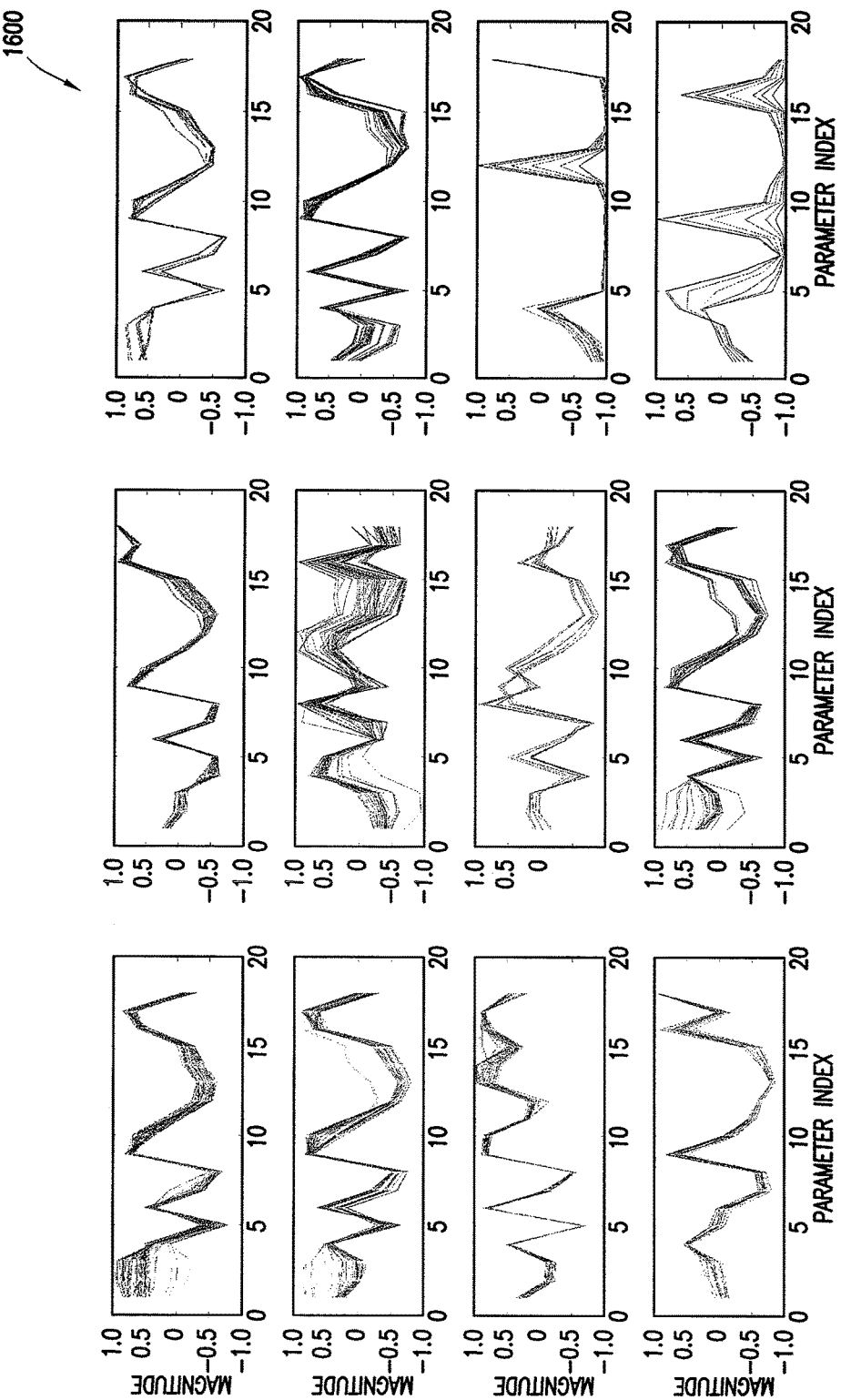
FIG. 17 is a graph set showing a tool response of 12 samples obtained from a second instrument, in accordance with certain embodiments of the present disclosure.

FIG. 16 illustrates a graph set 1500 showing a tool response of 12 samples obtained from the first instrument. FIG. 17 is a graph set 1600 showing a tool response of 12 samples obtained from the second instrument. The samples correspond to GOL10, RDT663, GOL08, GOL24, Naphthalene, Escaid110, Accolade, Toluene, CO2, RDT648, GOL25, CH4 displayed from left to right, top to bottom, with actual spectra interfered with artificial filter functions under environmental influence.

The filter temperature is 65° C. for the first instrument and the 147.5° C. for the second instrument. Note that the fabrication induced change and the jitter between the tools are also different. Each parameter of spectrometer response (18 parameters in total) is normalized between −1 and +1 for convenience. The transformation algorithm to convert the data in FIG. 16 to the data in FIG. 17 is developed through an 18-12-18 feed-forward neural network (18 inputs, 12 hidden neurons, 18 outputs) with randomly mixed samples as training, validation and testing data.

Figure 18:
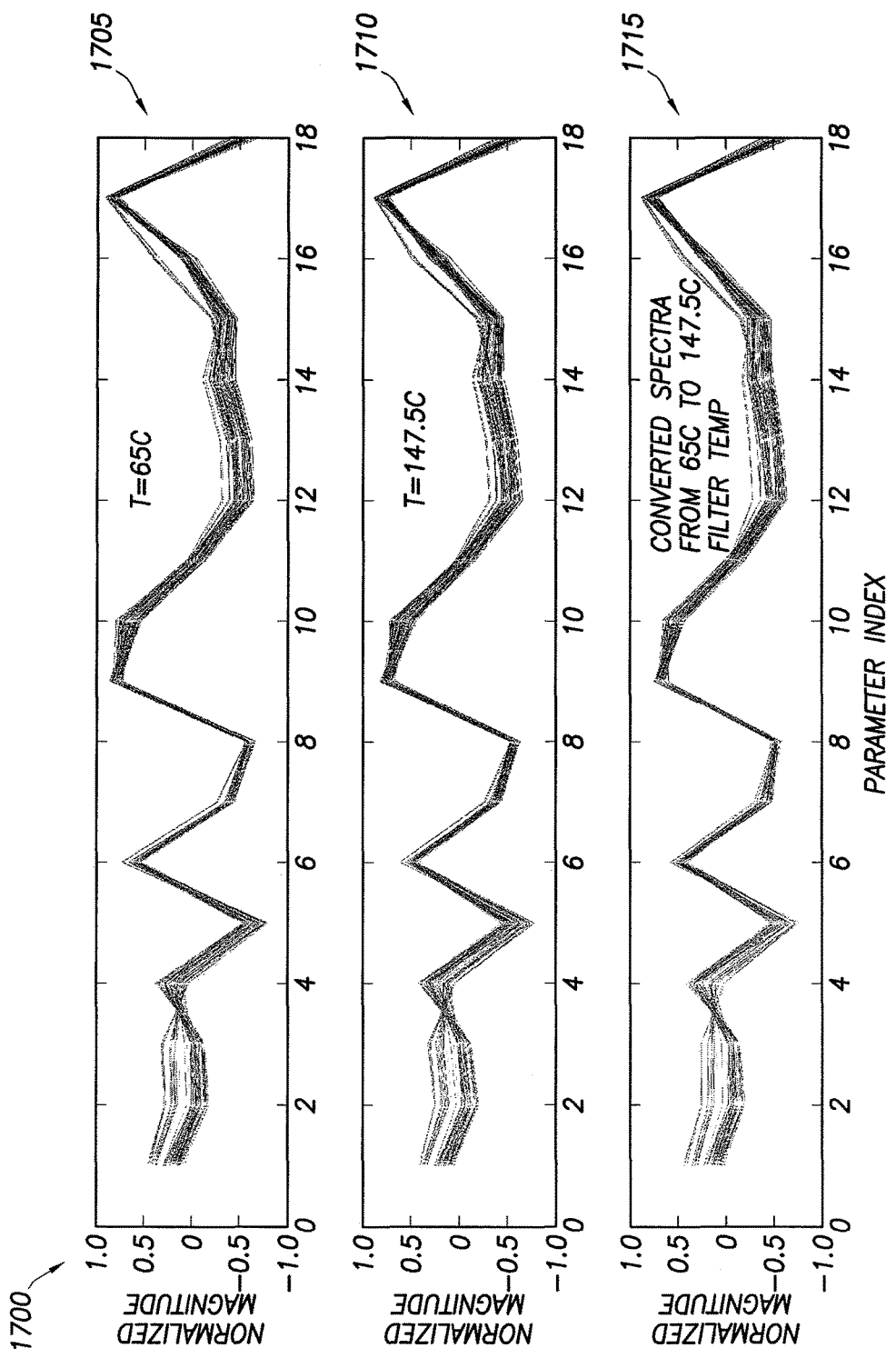
FIG. 18 is a graph set of testing sample response measured at a first instrument, a second instrument, and through conversion, in accordance with certain embodiments of the present disclosure.

FIG. 18 is a graph set 1700 of testing sample response measured at the first instrument, second instrument, and through conversion. The graph set 1700 shows the tool response of a novel testing sample (GOL11), which is measured at the first instrument corresponding to graph 1705, at the second instrument corresponding to graph 1710, and by using the transformation algorithm, which corresponds to graph 1715. Although in this example, to demonstrate the concept, the transformation algorithm is to convert response property between two spectrometers across two temperatures, the actual standardization can be implemented in different ways such as many to one, one to one, etc. The conversion can also be in two directions depending on application.

Figure 19:
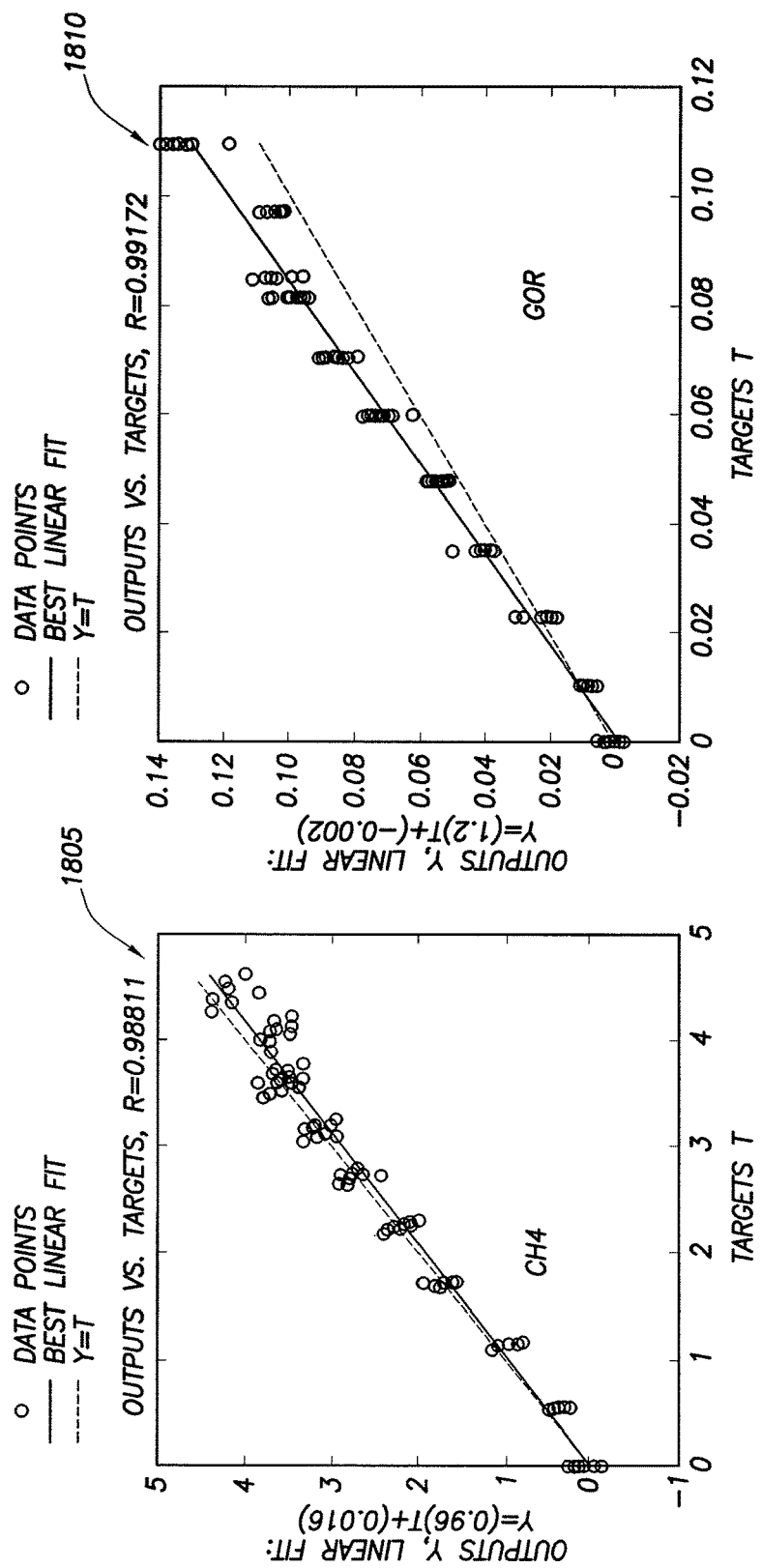
FIG. 19 illustrates graphs of predictions of unknown sample fluid components, presented using a local calibration model trained with all available 12 samples from a database of a second instrument, in accordance with certain embodiments of the present disclosure.

FIG. 19 illustrates predictions of unknown sample (GOL11) fluid components, presented using a local calibration model trained with all available 12 samples from the database of the second instrument. Graph 1805 illustrates the predictions as to CH4 and graph 1810 illustrates the predictions as to GOR. The unknown sample response is transformed to the second instrument first before putting it into the calibration model. The parameter of GOR is calculated as methane concentration CH4 divided by the sum of SARA in this example.

Figure 20:
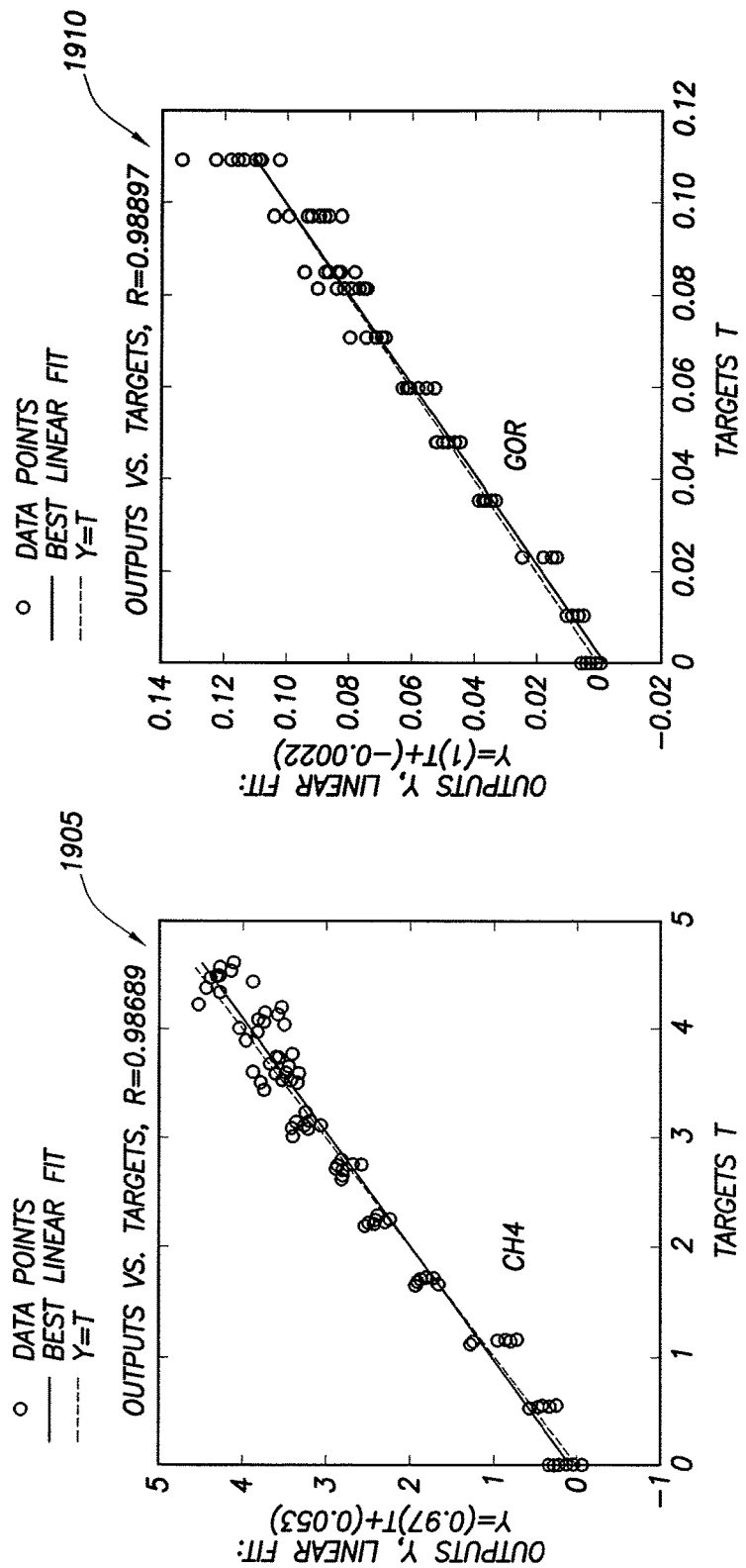
FIG. 20 illustrates graphs of predictions for the same parameters, but with the calibration model developed by applying a sample selection routine first, in accordance with certain embodiments of the present disclosure.

FIG. 20 illustrates predictions on the same parameters, but with the calibration model developed by applying a sample selection routine first. As a result, only 9 samples are selected to build a local calibration model, with Toluene, CO2 and GOL25 excluded. Graph 1905 illustrates the predictions as to CH4 and graph 1910 illustrates the predictions as to GOR. The improved prediction on GOR by using selected samples is observable. The calibration models used to produce results in FIG. 18 and FIG. 19 deploy a 19-10-10-5 neural network structure, which has two hidden layers with 10 neurons in each, and multiple outputs (MO) representing CH4 plus SARA. The number of inputs for these models is 19, including all 18 parameters from the spectrometer plus fluid density.

Figure 21:
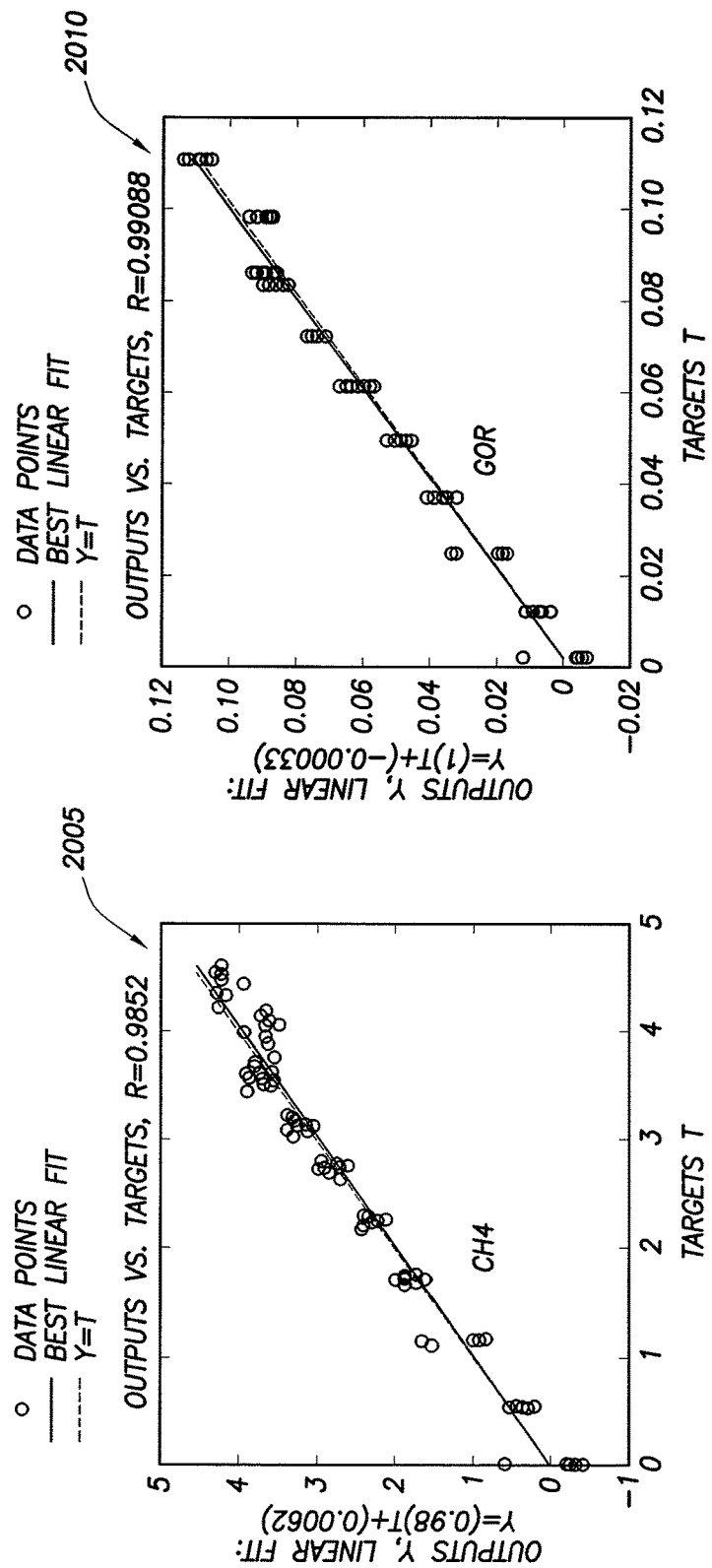
FIG. 21 illustrates graphs of further improved GOR prediction by using five single-output (SO) models, in accordance with certain embodiments of the present disclosure.

FIG. 21 presents further improved GOR prediction by using five single-output (SO) models. Graph 2005 illustrates the predictions as to CH4; graph 2010 illustrates the predictions as to GOR. Following a backward stepwise input selection procedure, each model has its own inputs determined from the tool response, and the summary table with RMS (root mean square) error on each output for testing sample is given in Table 2. Table 2 provides a summary of input selection for a single-output neural network calibration model trained on 9 samples and applied to GOL11 property prediction.

TABLE 2

Summary table of input selection for single-output neural network calibration model trained on 9 samples and applied to GOL11 property prediction.

| | CH4 | SATURATE | AROMATIC | RESIN | ASPHALTENIC |
|---|---|---|---|---|---|
| FLUID Density | | Y | Y | | Y |
| Filter 01 | Y | | Y | | |
| Filter 02 | | | | | |
| Filter 03 | | | | | Y |
| Filter 04 | Y | | Y | Y | Y |
| Filter 05 | Y | Y | Y | | Y |
| Filter 06 | Y | | Y | Y | Y |
| Filter 07 | Y | Y | Y | | Y |
| Filter 08 | Y | Y | Y | Y | Y |
| Filter 09 | Y | | | Y | Y |
| Filter 10 | | Y | Y | Y | Y |
| Filter 11 | Y | Y | Y | Y | Y |
| Filter 12 | | Y | | Y | Y |
| Filter 13 | Y | Y | Y | | Y |
| Filter 14 | | | Y | Y | Y |
| Filter 15 | Y | Y | Y | | |
| Filter 16 | | Y | Y | Y | |
| Filter 17 | Y | | Y | | Y |
| Filter 18 | | Y | Y | | |
| Pred. Error (rms) | 0.2448 (mol/L) | 0.0175 (g/mL) | 0.0109 (g/mL) | 0.0031 (g/mL) | 0.0077 (g/mL) |

It should be noted that, although transformation algorithms and calibration models are built with non-linear neural networks in this section for testing, the other linear and nonlinear modeling methods such as PLS and PCR can also be used separately or jointly with NN for this application. While certain embodiments may include array-filter spectrometer based calibration transfer, the teachings of the present disclosure may be employed with certain embodiments including Integrated Computational Element (ICE) as analogue or digital optical computation devices weather interference based, adsorption based or other appropriate wave form encoding method based, calibration transfer, particularly considering that ICE can be constructed as an interference filter for analyte-specific channels. The following methods may be implemented for function testing and response calibration of optical tools and may be applicable to both array-filter spectrometer and ICE photometer based applications in certain embodiments.

Figure 22:
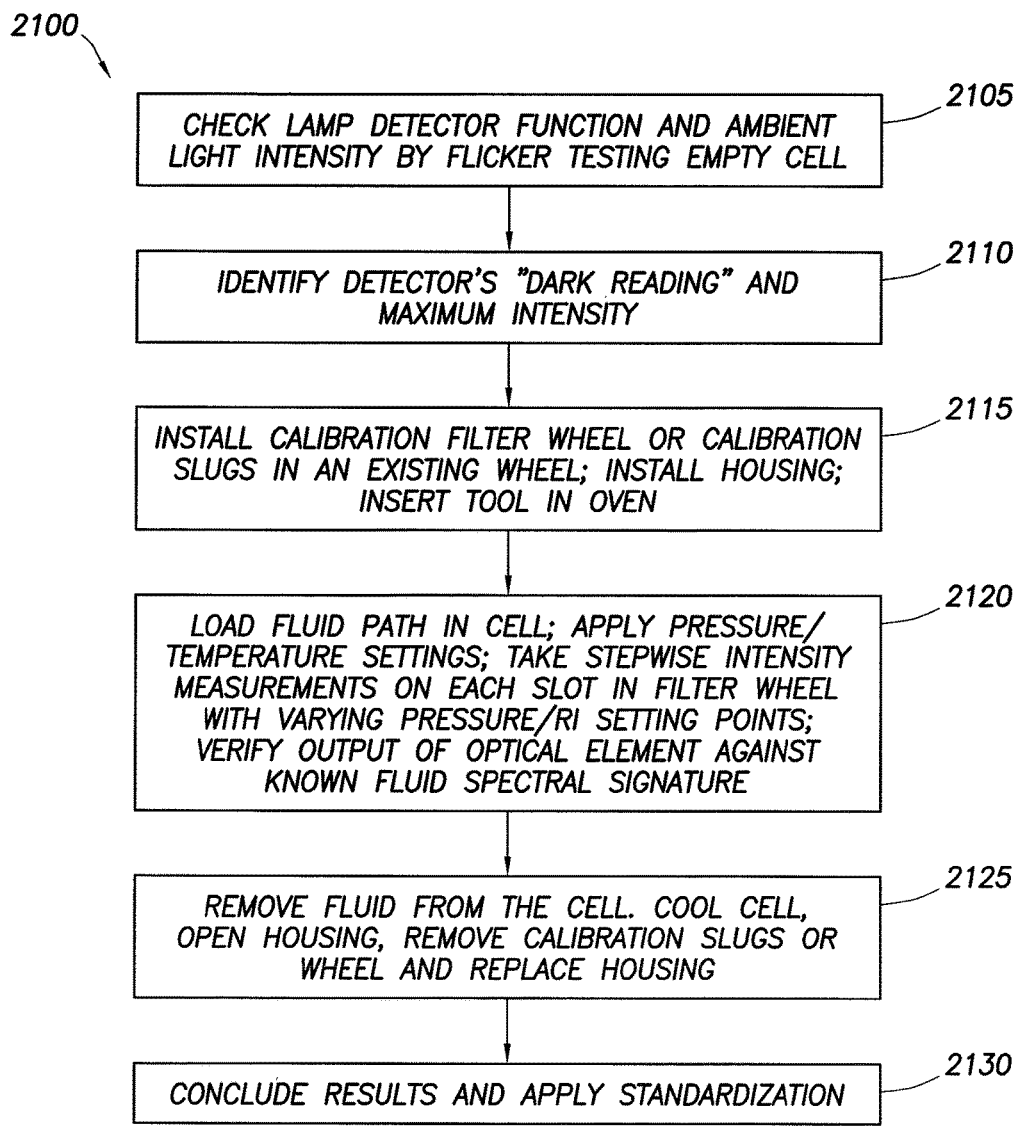
FIG. 22 is a flow chart illustrating a method of function testing and response calibration of optical tools applicable to both array-filter spectrometer and ICE based applications, in accordance with certain embodiments of the present disclosure.

FIG. 22 is a flow chart illustrating a method 2100 of function testing and response calibration of optical tools applicable to both array-filter spectrometer and ICE based applications, in accordance with certain embodiments of the present disclosure. As a non-limiting example, an optical tool may include all or part of apparatus 1, an optical sensor 18, and a light source 19, as previously described in reference to FIG. 3. According to one embodiment, method 2100 may begin, as indicated by block 2105, with checking a lamp detector function and ambient light intensity by flicker testing applied to an empty cell (e.g., without a filter in a detection axis). A detector response under background (ambient) light can be read with a lamp off.

As indicated by block 2110, the detector's "dark reading" and maximum intensity may be identified. The "dark reading" may be achieved by dropping black cloth over the tool with the lamp off. The maximum detector intensity may be obtained with the lamp on.

As indicated by block 2115, either a calibration filter wheel, such as the filter wheel 16, may be installed or calibration slugs in an existing wheel may be installed. Calibration slugs may be known spectral signatures for a component. A housing may be installed to ensure uniform tool conditions, and the tool may be put in an oven or other temperature-controllable environment.

As indicated by block 2120, a fluid path may be loaded in a cell. As a non-limiting example, this may correspond to establishing a sample fluid path with the sample line 39 of the optical cell 15. Pressure and temperature setting points may be applied to the fluid path. At each pressure step, an intensity measurement may be taken on each slot in the filter wheel. Then, temperature may be changed to the second setting point, and steps may be repeated. Since cell path changes as a function of pressure and temperature, and source intensity varies as a function of temperature and index of refraction (Ri), Ri may also be varied by using dense fluid, and the output of optical element can be verified against a known fluid spectral signature.

As indicated by block 2125, fluid may be removed from the cell. The cell may be cooled. The housing may be opened, and the calibration slugs or the wheel may be removed, and the housing may be replaced. Then, as indicated by block 2130, results may be concluded, and standardization may be applied according to methods described previously. Once an appropriate high temperature response for a second instrument is determined, then a set of room temperature responses may be measured such that a calibration transfer routine may be developed for a set of responses at room temperature on the first instrument to a set of higher temperatures on the second instrument by only making future measurements at room temperature. Although the description is described for room temperature versus high temperature, it is recognized that the process more generally applies to any state variable such as, but not limited to, temperature, pressure, and vibration level. Also, it is recognized that state condition for which the second instrument has a calibration transfer need not be at the exact state condition for which the measurements were made by the use of the linear and nonlinear extrapolation methods described herein.

In certain embodiments, a calibration wheel may be used in place of the sample cell. The calibration wheel may contain "standard samples" from which to transfer the calibration. Then, the sample cell may be either reinserted in the tool and measured for temperature, pressure, and index of refraction effects, or the effects are measured independently outside of the tool, and convoluted with the response of the standard calibration wheel. In addition, the standard calibration wheel may be incorporated into the tool such that the differential response through a fluid could be measured in an optical generalized standard addition manner analogous to chemical standard addition method. Note that this may yield no information about the fluid itself, but may lead to the normalization of the optical response in place and in use. Moreover, waveform response channels for ICE may be designed to be the equivalent to a calibration channel convoluted with an ICE or filter channels. Since the effects may be multiplicatively commutative wherever placed within the optical train, the calibration-response channel waveforms may all be placed in the response filter wheel, and all detector drift, temperature effects, index of refraction effects, etc. could be normalized out on the fly. As another embodiment, multiple ICE with different calibrations may be included within the wheel for normalization. Optical GSAM (General Standard Addition Method) standards may easily be placed at any convenient place within the optical path since the effects are multiplicative and commutative to a first order. Polarization effects which are not commutative may be taken advantage of with respect to combination effects allowing more GSAM levels per set of polarizing standards. Standards with polarization effects may still be placed at multiple places throughout the optical setup, however more care must be taken to track polarization effects. The process is convenient to optical methods. However, the process may be extended to other sensors so long as standards affecting the response of a sensor may be placed within the field of observation of that sensor. For instance, an inductive electrical sensor may have a standard placed within the field of the sensor during operation for an electrical GSAM calibration.

Accordingly, the present disclosure provides methods that may be applicable to both spectrometer-based and ICE-based calibration transfer, and may be implemented in a flexible manner to meet different service requirements. In certain embodiments, a hybrid solution method may be well defined and/or tested at each stage of the process to optimize the performance of downhole optical tool. In certain embodiments, a spectrometer to be used in a field instrument may be optimized with respect to filter selection by using mathematically perturbed spectra to simulate filter response under rugged environmental conditions. Therefore, the calibration transfer or standardization may be less sensitive to the filter manufacturing variation and environmental factors. Software-based simulation may be more realistic (by modeling blackbody effect, for example) based on testing data to ease calibration transfer or build robust calibration model without standardization. In certain embodiments, special neural network design with arbitrary neuron connection and feed-forward calculation only may be implemented for calibration transfer. This approach may reduce the number of coefficients of transformation algorithm significantly and may reduce the risk of over-fitting, while retaining the advantage of NN in flexible modeling of non-linear relationships. In certain embodiments, preliminary training sample selection may be implemented with a clustering algorithm first, followed by secondary backward stepwise selection to remove irrelevant samples and ensure that the local predictive model is calibrated with necessary and sufficient standard samples. Accordingly, certain embodiments according to the present disclosure may provide for advanced simulation and modeling technology, a robust transformation algorithm, and an integrated solution with quality control.

Even though the figures may depict embodiments of the present disclosure in a particular orientation, it should be understood by those skilled in the art that embodiments of the present disclosure are well suited for use in a variety of orientations. Accordingly, it should be understood by those skilled in the art that the use of directional terms such as above, below, upper, lower, upward, downward and the like are used in relation to the illustrative embodiments as they are depicted in the figures, the upward direction being toward the top of the corresponding figure and the downward direction being toward the bottom of the corresponding figure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are each defined herein to mean one or more than one of the elements that the article introduces.

What is claimed is:

1. A method of calibration transfer for a testing reservoir formation instrument, the method comprising:
    collecting a plurality of first samples;
    generating a plurality of standard responses of a first instrument based, at least in part, on the plurality of first samples;
    performing instrument standardization of a second reservoir formation instrument based, at least in part, on the plurality of standard responses of the first instrument;
    obtaining data corresponding to a second sample using the second reservoir formation instrument;
    building a calibration model based on a first subset of the plurality of first samples;
    identifying a component of the second sample based, at least in part, on the calibration model;
    performing a formation testing operation using the second reservoir formation instrument;
    acquiring a signal for at least one of the plurality of first samples at the second reservoir formation instrument;
    determining a response of the second reservoir formation instrument based on the acquired signal;
    transforming the response of the second reservoir formation instrument based, at least in part, on at least one of the plurality of standard responses of the first instrument, wherein the response of the second reservoir formation instrument is transformed to at least one of the plurality of standard responses of the first instrument based, at least in part, on one or more of temperature, vibration, and pressure; and
    adjusting the calibration model based, at least in part, on the transformed response of the second reservoir formation instrument.

2. The method of claim 1, further comprising:
    determining a parameter of the second sample based, at least in part, on the component of the second sample.

3. The method of claim 1, further comprising:
    determining a parameter of the second sample based, at least in part, on a General Standard Addition Method.

4. The method of claim 1, further comprising:
    applying a transformation algorithm to data corresponding to the second sample prior to identifying the component of the second sample.

5. The method of claim 1, wherein the calibration model is a single-output model.

6. The method of claim 1, wherein the calibration transfer is used to adjust one or more components of one or more of saturates, aromatics, resins, asphaltenes, methane, ethane, propane, butane, pentane, carbon dioxide, hydrogen sulfide, water, synthetic drilling fluid components, phase composition, density, API gravity, gas/oil ratio (GOR), and contamination.

7. The method of claim 1, wherein a signal from the first instrument is translated to a response function of the second reservoir formation instrument.

8. The method of claim 1, wherein the first instrument is a spectrometer.

9. The method of claim 1 wherein at least one of a first signal from the first instrument and the signal for the at least one of the plurality of first samples at the second reservoir formation instrument is an optical signal.

10. The method of claim 1, wherein the step of generating the plurality of standard responses of the first instrument comprises determining a property of interest, further comprising:
developing a transformation algorithm to adjust data corresponding to the property of interest based, at least in part, on the response of the second reservoir formation instrument; and
adjusting data corresponding to the property of interest, based on at least one of the response of the second reservoir formation instrument and the transformation algorithm.

11. The method of claim 1, wherein the step of generating the standard response of the first instrument comprises determining a property of interest, and wherein the step of transforming the response of the second reservoir formation instrument comprises:
selecting a transformation algorithm to adjust data corresponding to the property of interest based, at least in part, on the response of the second reservoir formation instrument; and
adjusting data corresponding to the property of interest based, at least in part, on the transformation algorithm.

12. The method of claim 11, wherein the transformation algorithm is a neural network transformation algorithm, a support vector machine (SVM), or a radial basis function with optical inputs.

13. The method of claim 1, wherein identifying the component of the second sample based, at least in part, on the calibration model comprises:
selecting a calibration training sample; and
developing the calibration model, at least in part, with the calibration training sample.

14. The method of claim 13, wherein developing the calibration model comprises:
one or more of training, validating, and testing based, at least in part, on the response of the second reservoir formation instrument and one or more of:
a neural network;
a partial least squares regression; and
a principal component regression.

15. The method of claim 1, wherein the step of generating the plurality of standard responses of the first instrument comprises determining a property of interest.

16. The method of claim 15, wherein the property of interest is a classification property.

17. The method of claim 1, further comprising:
analyzing the plurality of the first samples at the first instrument to determine a deterministic response.

18. The method of claim 17, wherein the deterministic response corresponds to optical density at a characteristic wavelength.

19. The method of claim 1, wherein the first instrument comprises an optical tool, wherein the optical tool comprises a detector, and wherein generating the standard response of the first instrument comprises:
checking at least one of a lamp detector function and an ambient light intensity of the optical tool;
identifying at least one of a dark reading and a maximum intensity of the detector;
placing the optical tool in a temperature-controllable environment;
directing a fluid through the optical tool; and
verifying an output of the optical tool against a known fluid spectral signature.

20. The method of claim 19, wherein the optical tool is selected from a group consisting of an array-filter spectrometer and an ICE (Integrated Computational Element) based application.

* * * * *